(12) United States Patent
Gobbi et al.

(10) Patent No.: US 7,056,932 B2
(45) Date of Patent: Jun. 6, 2006

(54) HETEROCYCLYL SUBSTITUTED 1-ALKOXY ACETIC ACID AMIDES

(75) Inventors: Luca Claudio Gobbi, Oberwil (CH); Katrin Groebke Zbinden, Basel (CH); Peter Mohr, Basel (CH); Ulrike Obst, Reinach (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/009,464

(22) Filed: Dec. 10, 2004

(65) Prior Publication Data

US 2005/0137168 A1 Jun. 23, 2005

(30) Foreign Application Priority Data

Dec. 19, 2003 (EP) .................. 03104822

(51) Int. Cl.
| | |
|---|---|
| A61K 31/454 | (2006.01) |
| A61K 31/444 | (2006.01) |
| C07D 413/12 | (2006.01) |
| C07D 239/70 | (2006.01) |
| C07D 271/06 | (2006.01) |

(52) U.S. Cl. .............. 514/317; 514/335; 514/338; 514/341; 514/349; 514/350; 514/364; 514/374; 514/383; 514/394; 514/406; 514/414; 514/416; 514/417; 546/201; 546/268.1; 546/272.1; 546/275.4; 546/275.7; 546/293; 546/297; 546/298; 548/110; 548/128; 548/234; 548/262.8; 548/309.7; 548/375.1; 548/466; 548/472; 548/477

(58) Field of Classification Search .............. None
See application file for complete search history.

(56) References Cited

U.S. PATENT DOCUMENTS

| | | | |
|---|---|---|---|
| 5,084,466 A | | 1/1992 | Alig et al. |
| 5,256,812 A | | 10/1993 | Alig et al. |
| 5,399,585 A | | 3/1995 | Alig et al. |
| 5,498,778 A | * | 3/1996 | Carr et al. ............ 514/309 |
| 6,140,353 A | | 10/2000 | Ackermann et al. |

FOREIGN PATENT DOCUMENTS

| | | |
|---|---|---|
| EP | 0 921 116 | 6/1999 |
| EP | 1 364 960 | 11/2003 |
| WO | WO 00/35858 | 6/2000 |
| WO | WO 01/90051 | 11/2001 |
| WO | WO 2004/048335 | 6/2004 |
| WO | WO 2004/048335 | * 10/2004 |

OTHER PUBLICATIONS

Banner et al., STN International (2005) HCAPLU Database, Accession No. 2004:467862, Reg. No. 701265-25-0.*
Hilpert K., et al., *Design and Synthesis of Potent and Highly Selective Thrombin Inhibitors*, Journal of Medicinal Chemistry, American Chemical Society, Washington, US, vol. 37, No. 23 pp. 3889-3901 (1994), XP000561935.
Heran C., et al., *Antithrombotic Efficacy of RPR208566, A Novel Factor Xa Inhibitor, in a Rat Model of Carotid Artery Thrombosis*, European Journal of Pharmacology, Amsterdam, NL, vol. 389, pp. 201-207 (2000), XP002964258.

* cited by examiner

Primary Examiner—Kamal A. Saeed
Assistant Examiner—Andrew B. Freistein
(74) Attorney, Agent, or Firm—George W. Johnston; Patricia S. Rocha-Tramaloni

(57) ABSTRACT

The invention is concerned with novel heterocyclyl substituted 1-alkoxy acetic acid derivatives of formula (I)

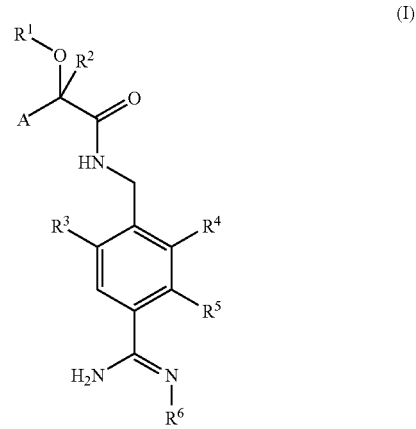

(I)

wherein $R^1$ to $R^6$ and A are as defined in the description and in the claims, as well as physiologically acceptable salts thereof. These compounds inhibit the formation of coagulation factors Xa, IXa and thrombin induced by factor VIIa and tissue factor and can be used as medicaments.

21 Claims, No Drawings

HETEROCYCLYL SUBSTITUTED 1-ALKOXY ACETIC ACID AMIDES

BACKGROUND OF THE INVENTION

The invention is concerned with novel heterocyclyl substituted 1-alkoxy acetic acid amides of the formula (I)

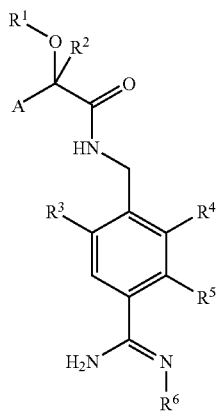

(I)

wherein $R^1$, $R^2$, $R^3$, $R^4$, $R^5$, $R^6$ and A are as described herewithin.

Further, the invention is concerned with a process for the manufacture of the above compounds, pharmaceutical preparations which contain such compounds as wellas the use of these compounds for the production of pharmaceutical preparations.

The compounds of formula (I) are active compounds and inhibit the formation of coagulation factors Xa, IXa and thrombin induced by factor VIIa and tissue factor or are derivatives which are converted under physiological conditions to such active compounds. These compounds consequently influence both platelet aggregation which is induced by these factors and plasmatic blood coagulation. They therefore inhibit the formation of thrombi and can be used for the treatment and/or prevention of diseases, such as arterial and venous thrombosis, deep vein thrombosis, pulmonary embolism, unstable angina pectoris, cardiac infarction, stroke due to atrial fibrillation, inflammation and arteriosclerosis. Furthermore, these compounds have an effect on tumour cells and prevent metastases. They can therefore also be used as antitumour agents.

Inhibitors of factor VIIa had previously been suggested for the inhibition of the formation of thrombi and for the treatment of related diseases (WO 00/35858 and WO 01/90051). However, there is still a need for novel factor VIIa inhibitors which exhibit improved pharmacological properties.

SUMMARY OF THE INVENTION

The present invention provides a new class of compounds of formula (I)

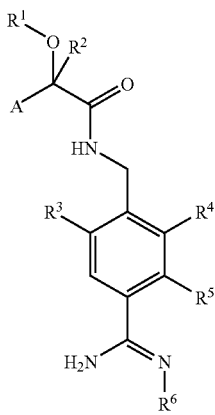

(I)

wherein

A is a heterocyclyl selected from the group consisting of pyrazolyl, triazolyl, 1-oxo-1,3-dihydro-isoindolyl, 1,3-dioxo-1,3-dihydro-isoindolyl, oxazolyl, benzimidazolyl, 1,2,4-oxadiazol-5-yl and 2-oxo-2H-pyridinyl, which heterocyclyl is optionally substituted with 1 to 3 substituents independently selected from the group consisting of aryl-$C_{1-7}$alkyl-O—$C_{1-7}$-alkyl, lower-alkyl, lower-alkoxy, halogen, aryl, aryl-lower-alkyl, heteroaryl-lower-alkyl, heteroaryl, heterocyclyl, tri-lower-alkyl-silanyl-lower-alkoxy-lower-alkyl, lower-alkyl-SO$_2$—NH, aryl-lower-alkyl-SO$_2$—NH, aryl-SO$_2$—NH, lower-alkyl-CO—NH, aryl-lower-alkyl-CO—NH, aryl-CO—NH, aryl-NH, and heteroaryl-NH, $R^1$ is lower-alkyl, $R^2$ is H or lower-alkyl, $R^3$, $R^4$ and $R^5$ independently from each other are selected from the group consisting of $C_{1-7}$alkyl-NH, hydrogen, halogen, carbamoyl-lower-alkoxy, carboxy-lower-alkoxy, carboxy-lower-alkyl-NH, lower-alkoxy-CO-lower-alkoxy, lower-alkoxy-CO-lower-alkyl-NH, carbamoyl-lower-alkyl-NH, lower-alkyl-NH—CO-lower-alkoxy, lower-alkyl-NH—CO-lower-alkyl-NH, aryl-NH—CO-lower-alkoxy, aryl-NH—CO-lower-alkyl-NH, carboxy-lower-alkyl-NH—CO-lower-alkoxy, carboxy-lower-alkyl-NH—CO-lower-alkyl-NH, lower-alkoxy-CO-lower-alkyl-NH—CO-lower-alkoxy, lower-alkoxy-CO-lower-alkyl-NH—CO-lower-alkyl-NH, aryloxy, aryl-NH, aryl-NH—CO—NH, aryl-O—CO—NH, aryl-lower-alkoxy, aryl-lower-alkyl-NH, aryl-lower-alkyl-NH—CO—NH, aryl-lower-alkoxy-CO—NH, heteroaryloxy, heteroaryl-NH, heteroaryl-NH—CO—NH, heteroaryl-O—CO—NH, heteroaryl-lower-alkoxy, heteroaryl-lower-alkyl-NH, heteroaryl-lower-alkyl-NH—CO—NH, heteroaryl-lower-alkoxy-CO—NH, aryl-CO—NH, heteroaryl-CO—NH, aryl-lower-alkyl-CO—NH, and heteroaryl-lower-alkyl-CO—NH, $R^6$ is hydrogen, hydroxy, aryl-lower-alkoxy-carbonyl, aryl-carbonyl, or aryloxy-carbonyl, or $R^5$ and $R^6$ are bound together to form a ring and —$R^5$—$R^6$— is —O— or —NH—, and pharmaceutically acceptable salts thereof.

These compounds unexpectedly are factor VIIa inhibitors. Furthermore, the compounds of the present invention exhibit improved pharmacological properties compared to the known compounds.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl. Lower-alkyl groups can optionally be substituted, e.g. by hydroxy. Such substituted lower-alkyl-groups are referred to as "hydroxy-lower-alkyl". Other possible optional substituents are e.g. halogen. Unsubstituted lower-alkyl groups are preferred.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$ The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O, The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and 2 to 20, preferably 2 to 16 carbon atoms, more preferrably 2 to 10 carbon atoms. Lower-alkenyl groups as described below also are preferred alkenyl groups. The term "lower-alkenyl" refers to a straight-chain or branched hydrocarbon residue comprising an olefinic bond and 2 to 7, preferably 2 to 4 carbon atoms, such as e.g. 2-propenyl.

The term "alkinyl", alone or in combination with other groups, stands for a straight-chain or branched hydrocarbon residue comprising a tripple bond and up to 20, preferably up to 16 carbon atoms. The term "lower-alkinyl" refers to a straight-chain or branched hydrocarbon residue comprising a tripple bond and 2 to 7, preferably 2 to 4 carbon atoms, such as e.g. 2-propinyl. Lower-alkinyl groups can be substituted, e.g. by hydroxy.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl" relates to the phenyl or naphthyl group, preferably the phenyl group, which can optionally be substituted by 1 to 5, preferably 1 to 3, substituents independently selected from the group consisting of lower-alkenyl, lower-alkinyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl, lower-alkyl-CO—NH, lower-alkyl-SO$_2$—NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy, benzyloxy-lower-alkoxy, and lower alkyl, which -lower-alkyl can optionally be substituted with halogen, hydroxy, $NH_2$, N(H, lower-alkyl) or N(lower-alkyl)$_2$. Preferred substituents are halogen, hydroxy, lower-alkyl, lower-alkoxy, benzyloxy, $NH_2$, lower-alkyl-CO—NH, lower-alkyl-SO$_2$—NH, lower-alkoxy-carbonyl-lower-alkoxy, carboxy-lower-alkoxy, carbamoyl-lower-alkoxy.

The term "aryloxy" refers to the group aryl-O—.

The term "heterocyclyl" as used herein denotes aromatic or non aromatic monocyclic heterocycles with 5 to 6 ring members or bicyclic heterocycles with 9 to 10 ring members, which comprise 1, 2 or 3 hetero atoms selected from nitrogen, oxygen and sulfur. Preferred heterocycles are pyrazolyl, triazolyl, 1-oxo-1,3-dihydro-isoindolyl, 1,3-dioxo-1,3-dihydro-isoindolyl, oxazolyl, benzimidazolyl, and 2-oxo-2H-pyridinyl. A heterocyclyl group may be substituted, e.g. as described earlier in connection with the term "aryl". Other preferred substituents are e.g. lower-alkyl, lower-alkoxy, halogen, aryl, aryl-lower-alkyl, heteroaryl-lower-alkyl, heteroaryl, tri-lower-alkyl-silanyl-lower-alkoxy-lower-alkyl, lower-alkyl-SO$_2$—NH, aryl-lower-alkyl-SO$_2$—NH, aryl-SO$_2$—NH, lower-alkyl-CO—NH, aryl-lower-alkyl-CO—NH, aryl-CO—NH, aryl-NH, and heteroaryl-NH.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridyl, oxo-pyridinyl, pyridazinyl, pyrimidinyl, pyrazinyl, thienyl, isoxazolyl, oxazolyl, oxadiazolyl, imidazolyl, pyrrolyl, tetrazolyl, benzoimidazolyl, indolyl. Preferred heteroaryl groups are pyridinyl, oxo-pyridinyl, thienyl, furyl, oxadiazolyl, pyrimidinyl, benzoimidazolyl, indolyl, more preferably pyridinyl. A heteroaryl group may be substituted, e.g. as described earlier in connection with the term "aryl". Unsubstituted heteroaryl groups are preferred.

The term "heteroaryloxy" refers to the group heteroaryl-O—.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Acid addition salts as described above are preferred.

DETAILED DESCRIPTION OF THE INVENTION

In detail, the present invention relates to compounds of formula (I)

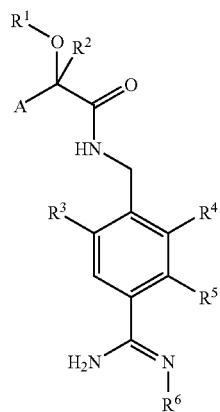

wherein

A is a heterocyclyl selected from the group consisting of pyrazolyl, triazolyl, 1-oxo-1,3-dihydro-isoindolyl, 1,3-dioxo-1,3-dihydro-isoindolyl, oxazolyl, benzimidazolyl, 1,2,4-oxadiazol-5-yl and 2-oxo-2H-pyridinyl, which heterocyclyl is optionally substituted with 1 to 3 substituents independently selected from the group consisting of aryl-$C_{1-7}$alkyl-O—$C_{1-7}$-alkyl, lower-alkyl, lower-alkoxy, halogen, aryl, aryl-lower-alkyl, heteroaryl-lower-alkyl, heteroaryl, heterocyclyl, tri-lower-alkyl-silanyl-lower-alkoxy-lower-alkyl, lower-alkyl-SO$_2$—NH, aryl-lower-alkyl-SO$_2$—NH, aryl-SO$_2$—NH, lower-alkyl-CO—NH, aryl-lower-alkyl-CO—NH, aryl-CO—NH, aryl-NH, and heteroaryl-NH, $R^1$ is lower-alkyl, $R^2$ is H or lower-alkyl, $R^3$, $R^4$ and $R^5$ independently from each other are selected from the group consisting of $C_{1-7}$alkyl-NH, hydrogen, halogen, carbamoyl-lower-alkoxy, carboxy-lower-alkoxy, carboxy-lower-alkyl-NH, lower-alkoxy-CO-lower-alkoxy, lower-alkoxy-CO-lower-alkyl-NH, carbamoyl-lower-alkyl-NH, lower-alkyl-NH—CO-lower-alkoxy, lower-alkyl-NH—CO-lower-alkyl-NH, aryl-NH—CO-lower-alkoxy, aryl-NH—CO-lower-alkyl-NH, carboxy-lower-alkyl-NH—CO-lower-alkoxy, carboxy-lower-alkyl-NH—CO-lower-alkyl-NH, lower-alkoxy-CO-lower-alkyl-NH—CO-lower-alkoxy, lower-alkoxy-CO-lower-alkyl-NH—CO-lower-alkyl-NH, aryloxy, aryl-NH, aryl-NH—CO—NH, aryl-O—CO—NH, aryl-lower-alkoxy, aryl-lower-alkyl-NH, aryl-lower-alkyl-NH—CO—NH, aryl-lower-alkoxy-CO—NH, heteroaryloxy, heteroaryl-NH, heteroaryl-NH—CO—NH, heteroaryl-O—CO—NH, heteroaryl-lower-alkoxy, heteroaryl-lower-alkyl-NH, heteroaryl-lower-alkyl-NH—CO—NH, heteroaryl-lower-alkoxy-CO—NH, aryl-CO—NH, heteroaryl-CO—NH, aryl-lower-alkyl-CO—NH, and heteroaryl-lower-alkyl-CO—NH, $R^6$ is hydrogen, hydroxy, aryl-lower-alkoxy-carbonyl, aryl-carbonyl, or aryloxy-carbonyl, or $R^5$ and $R^6$ are bound together to form a ring and —$R^5$—$R^6$— is —O— or —NH—, and pharmaceutically acceptable salts thereof.

The compounds of formula (I) have at least one asymmetric C atom and can therefore exist as an enantiomeric mixture, diastereomeric mixture or as optically pure compounds.

Compounds of formula (I) can exist in tautomeric forms and the invention encompasses all such tautomeric forms. In particular, the substituent $R^6$ can be exchanged with a hydrogen atom bound to the other nitrogen atom of the amidino (carbamimidoyl) group.

Compounds of formula (I) are individually preferred and physiologically acceptable salts thereof are individually preferred, with the compounds of formula (I) being particularly preferred.

A preferred embodiment of the present invention relates to compounds of formula (I) as described above, wherein A is a heterocyclyl selected from the group consisting of pyrazolyl, triazolyl, 1,3-dioxo-1,3-dihydro-isoindolyl, oxazolyl, benzimidazolyl, and 2-oxo-2H-pyridinyl, which heterocyclyl is optionally substituted with 1 to 3 substituents independently selected from the group consisting of lower-alkyl, aryl, aryl-lower-alkyl, heteroaryl, tri-lower-alkyl-silanyl-lower-alkoxy-lower-alkyl, aryl-lower-alkyl-SO$_2$—NH, aryl-SO$_2$—NH, aryl-NH, and heteroaryl-NH.

A more preferred embodiment of the present invention relates to compounds of formula (I) as described above, wherein A is pyrazolyl which is substituted with 1 to 2 substituents independently selected from the group consisting of lower-alkyl, aryl, aryl-lower-alkyl and heteroaryl, or A is triazolyl which is substituted with 1 to 2 substituents independently selected from the group consisting of lower-alkyl and aryl, or A is 1,3-dioxo-1,3-dihydro-isoindolyl, or A is oxazolyl which is substituted with aryl, or A is benzimidazolyl which is optionally substituted with lower-alkyl or tri-lower-alkyl-silanyl-lower-alkoxy-lower-alkyl, or A is 2-oxo-2H-pyridinyl which is substituted with lower-alkyl, aryl, aryl-lower-alkyl-SO$_2$—NH, aryl-SO$_2$—NH, aryl-NH, or heteroaryl-NH.

Compounds of formula (I) as described above, wherein

A is pyrazolyl which is substituted with 1 to 2 substituents independently selected from the group consisting of lower-alkyl, aryl and heteroaryl, or A is triazolyl which is substituted with aryl, or A is 1,3-dioxo-1,3-dihydro-isoindolyl, or A is 2-oxo-2H-pyridinyl which is substituted with aryl, aryl-lower-alkyl-SO$_2$—NH, aryl-NH, or heteroaryl-NH, are more preferred, with those compounds wherein A is 3-(5-chloro-2-hydroxy-phenyl)-pyrazol-1-yl, 3-pyridin-4-yl-pyrazol-1-yl, 3-phenyl-[1,2,4]triazol-1-yl, 3-(2-hydroxy-phenyl)-4-methyl-pyrazol-1-yl, 1,3-dioxo-1,3-dihydro-isoindol-2-yl, 2-oxo-3-phenylmethanesulfonylamino-2H-pyridin-1-yl, 2-oxo-3-(pyridin-3-ylamino)-2H-pyridin-1-yl, 2-oxo-3-phenylamino-2H-pyridin-1-yl, or 2-oxo-6-phenyl-1,2-dihydro-pyridin-3-yl being particularly preferred.

Preferred compounds of formula (I) are those, wherein $R^1$ is methyl or ethyl, preferably those, wherein $R^1$ is ethyl. Another preferred embodiment of the present invention relates to compounds of formula (I) as described above, wherein $R^2$ is hydrogen.

In a further preferred embodiment, the invention relates to compounds of formula (I) as described above in which $R^3$, $R^4$ and $R^5$ independently from each other are selected from the group consisting of hydrogen, halogen, and carbamoyl-lower-alkoxy. Preferably, $R^3$ is hydrogen or halogen, more preferably hydrogen. Compounds wherein $R^4$ is hydrogen, halogen, or carbamoyl-lower-alkoxy are also preferred, with those compounds wherein $R^4$ is hydrogen, fluorine, or carbamoyl-methoxy being particularly preferred.

The invention embraces especially compounds in accordance with the above definitions in which wherein $R^5$ is hydrogen or halogen, preferably those wherein $R^5$ is hydrogen.

In another preferred embodiment $R^6$ is hydrogen, hydroxy, or aryl-lower-alkoxy-carbonyl, more preferably $R^6$ is hydrogen. Moreover, the invention relates especially to compounds of formula (I) as defined above wherein $R^5$ and $R^6$ are bound together and —$R^5$—$R^6$— is —O— or —NH—. Such compounds are characterised by formula (Ia) and (Ib) respectively.

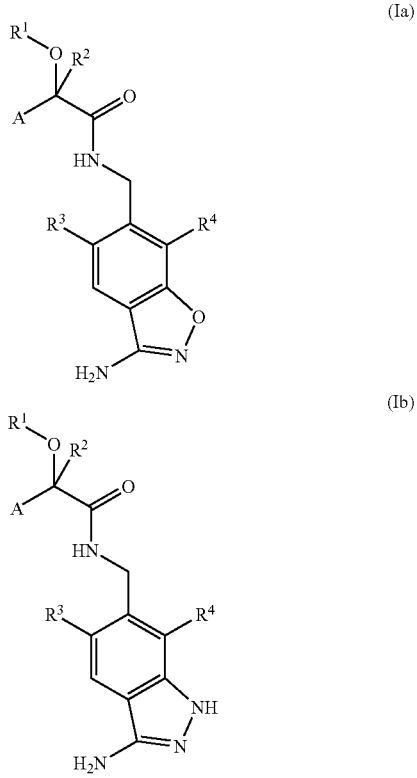

(Ia)

(Ib)

In particular, preferred compounds are the compounds of formula (I) described in the examples as individual compounds as well as pharmaceutically acceptable salts thereof.

Preferred compounds of formula (I) are those selected from the group consisting of (RS)-N-(4-carbamimidoyl-benzyl)-2-ethoxy-2-[3-(4-methoxy-phenyl)-pyrazol-1-yl]-acetamide hydrochloride, (RS)-N-(4-carbamimidoyl-benzyl)-2-ethoxy-2-(3-phenyl-pyrazol-1-yl)-acetamide hydrochloride, (RS)-N-(4-carbamimidoyl-benzyl)-2-ethoxy-2-(5-methyl-3-pyridin-3-yl-pyrazol-1-yl)-acetamide acetate, (RS)-2-[3-(2-benzyloxy-5-chloro-phenyl)-pyrazol-1-yl]-N-(4-carbamimidoyl-benzyl)-2-ethoxy-acetamide hydrochloride, (RS)-N-(4-carbamimidoyl-benzyl)-2-[3-(5-chloro-2-hydroxy-phenyl)-pyrazol-1-yl]-2-ethoxy-acetamide hydrochloride, (RS)-2-[3-(3-amino-phenyl)-pyrazol-1-yl]-N-(4-carbamimidoyl-benzyl)-2-ethoxy-acetamide hydrochloride, (RS)-2-[3-(3-acetylamino-phenyl)-pyrazol-1-yl]-N-(4-carbamimidoyl-benzyl)-2-ethoxy-acetamide hydrochloride, (RS)-N-(4-carbamimidoyl-benzyl)-2-ethoxy-2-[3-(3-methanesulfonylamino-phenyl)-pyrazol-1-yl]-acetamide hydrochloride, (RS)-[amino-(4-{[2-ethoxy-2-(3-pyridin-4-yl-pyrazol-1-yl)-acetylamino]-methyl}-phenyl)-methylene]-carbamic acid benzyl ester, (RS)-N-(4-carbamimidoyl-benzyl)-2-ethoxy-2-(3-pyridin-4-yl-pyrazol-1-yl)-acetamide acetate, (RS)-2-ethoxy-N-[4-(N-hydroxycarbamimidoyl)-benzyl]-2-(3-phenyl-[1,2,4]triazol-1-yl)-acetamide, (RS)-N-(4-carbamimidoyl-benzyl)-2-ethoxy-2-(3-phenyl-[1,2,4]triazol-1-yl)-acetamide acetate, (RS)-2-[3-(2-benzyloxy-phenyl)-4-methyl-pyrazol-1-yl]-2-ethoxy-N-[4 -(N-hydroxycarbamimidoyl)-benzyl]-acetamide, (RS)N-(4-carbamimidoyl-benzyl)-2-ethoxy-2-[3-(2-hydroxy-phenyl)-4-methyl-pyrazol-1-yl]-acetamide acetate, (RS)-N-(4-carbamimidoyl-benzyl)-2-[3-(2-carbamoyl-methoxy-phenyl)-4-methyl-pyrazol-1-yl]-2-ethoxy-acetamide acetate, (RS)-[2-(1-{ethoxy-[4-(N-hydroxycarbamimidoyl)-benzylcarbamoyl]-methyl}-4-methyl-1H-pyrazol-3-yl)-phenoxy]-acetic acid ethyl ester, (RS)-(2-{1-[(4-carbamimidoyl-benzylcarbamoyl)-ethoxy-methyl]-4-methyl-1H-pyrazol-3-yl}-phenoxy)-acetic acid ethyl ester acetate, (RS)-(2-{1-[(4-carbamimidoyl-benzylcarbamoyl)-ethoxy-methyl]-4-methyl-1H-pyrazol-3-yl}-phenoxy)-acetic acid acetate, (RS)-[1-amino-1-(4-{[2-(1,3-dioxo-1,3-dihydro-isoindol-2-yl)-2-ethoxy-acetylamino]-methyl}-phenyl)-meth-(Z)-ylidene]-carbamic acid benzyl ester, (RS)-N-(4-carbamimidoyl-benzyl)-2-(1,3-di oxo-1,3-dihydro-isoindol-2-yl)-2-ethoxy-acetamide acetate, (RS)-2-(1-benzyl-1H-pyrazol-3-yl)-N-(4-carbamimidoyl-benzyl)-2-methoxy-acetamide hydrochloride, (RS)-N-(4-carbamimidoyl-benzyl)-2-ethoxy-2-(2-phenyl-oxazol-4-yl)-acetamide acetate, (RS)-2-ethoxy-N-[4-(N-hydroxycarbamimidoyl)-benzyl]-2-(5-methyl-1-phenyl -1H-[1,2,4]triazol-3-yl)-acetamide, (RS)-N-(4-carbamimidoyl-benzyl)-2-ethoxy-2-(5-methyl-1-phenyl-1H-[1,2,4]triazol-3-yl)-acetamide acetate, (RS)-N-(4-carbamimidoyl-benzyl)-2-methoxy-2-(1-methyl-1H-benzoimidazol-2-yl)-acetamide acetate, (RS)-[1-amino-1-[4-({2-methoxy-2-[1-(2-trimethylsilanyl-ethoxymethyl)-1H-benzoimidazol-2-yl]-acetylamino}-methyl)-phenyl]-meth-(E)-ylidene]-carbamic acid benzyl ester, (RS)-[1-amino-1-(4-{[2-(1H-benzoimidazol-2-yl)-2-methoxy-acetylamino]-methyl}-phenyl)-meth-(E)-ylidene]-carbamic acid benzyl ester, (RS)-2-(1H-benzoimidazol-2-yl)-N-(4-carbamimidoyl-benzyl)-2-methoxy-acetamide acetate, (RS)-N-(4-carbamimidoyl-benzyl)-2-ethoxy-2-(2-oxo-3-phenylmethanesulfonylamino-2H-pyridin-1-yl)-acetamide acetate, (RS)-2-(3-benzenesulfonylamino-2-oxo-2H-pyridin-1-yl)-N-(4-carbamimidoyl-benzyl)-2-ethoxy-acetamide acetate, (RS)-N-(4-carbamimidoyl-benzyl)-2-ethoxy-2-(2-oxo-3-phenylamino-2H-pyridin-1-yl)-acetamide acetate, (RS)-{amino-[4-({2-ethoxy-2-[3-(3-methoxy-phenylamino)-2-oxo-2H-pyridin-1-yl]-acetyl amino}-methyl)-phenyl]-methylene}-carbamic acid benzyl ester, (RS)-N-(4-carbamimidoyl-benzyl)-2-ethoxy-2-[3-(3-methoxy-phenylamino)-2-oxo-2H-pyridin-1-yl]-acetamide acetate, (RS)-{amino-[4-({2-ethoxy-2-[3-(3-fluoro-phenylamino)-2-oxo-2H-pyridin-1-yl]-acetylamino}-methyl)-phenyl]-methylene}-carbamic acid benzyl ester, (RS)-N-(4-carbamimidoyl-benzyl)-2-ethoxy-2-[3-(3-fluoro-phenylamino)-2-oxo-2H-pyridin-1-yl]-acetamide acetate, (RS)-{amino-[4-({2-ethoxy-2-[2-oxo-3-(pyridin-3-ylamino)-2H-pyridin-1-yl]-acetylamino}-methyl)-phenyl]-methylene}-carbamic acid benzyl ester, (RS)-N-(4-carbamimidoyl-benzyl)-2-ethoxy-2-[2-oxo-3-(pyridin-3-ylamino)-2H-pyridin-1-yl]-acetamide acetate, (RS)-N-[2-chloro-4-(N-hydroxycarbamimidoyl)-benzyl]-2-ethoxy-2-(2-oxo-3-phenylamino-2H-pyridin-1-yl)-acetamide, (RS)-N-(4-carbamimidoyl-2-chloro-benzyl)-2-ethoxy-2-(2-oxo-3-phenylamino-2H-pyridin-1-yl)-acetamide acetate, (RS)-N-[3-chloro-4-(N-hydroxycarbamimidoyl)-benzyl]-2-ethoxy-2-(2-oxo-3-phenylamino-2H-pyridin-1-yl)-acetamide, (RS)-N-(4-carbamimidoyl-3-chloro-benzyl)-2-ethoxy-2-(2-oxo-3-phenylamino-2H-pyridin-1-yl)-acetamide acetate, (RS)-2-ethoxy-N-[2-fluoro-4-(N-hydroxycarbamimidoyl)-benzyl]-2-(2-oxo-3-phenylamino-2H-pyridin-1-yl)-acetamide, (RS)-N-(4-carbamimidoyl-2-fluoro-benzyl)-2-ethoxy-2-(2-oxo-3-phenylamino-2H-pyridin-1-yl)-acetamid acetate, (RS)-2-ethoxy-N-[3-fluoro-4-(N-hydroxycarbamimidoyl)-benzyl]-2-(2-oxo-3-phenylamino-2H-pyridin-1-yl)-acetamide, (RS)-N-(4-carbamimidoyl-3-fluoro-benzyl)-2-ethoxy-2-(2-oxo-3-phenylamino-2H-pyridin-1-yl)-acetamide acetate, (RS)-N-[2,6-difluoro-4-(N-hydroxycarbamimidoyl)-benzyl]-2-ethoxy-2-(2-oxo-3-phenylamino-2H-pyridin-1-yl)-acetamide, (RS)-N-(4-carbamimidoyl-2,6-difluoro-benzyl)-2-ethoxy-2-(2-oxo-3-phenylamino-2H-pyridin-1-yl)-acetamide acetate, (RS)-N-(3-amino-benzo[d]isoxazol-6-ylmethyl)-2-ethoxy-2-(2-oxo-3-phenylamino-2H-pyridin-1-yl)-acetamide, (RS)-N-(3-amino-1H-indazol-6-ylmethyl)-2-ethoxy-2-(2-oxo-3-phenylamino-2H-pyridin-1-yl)-acetamide, (RS)-N-[2-carbamoylmethoxy-4-(N-hydroxycarbamimidoyl)-benzyl]-2-ethoxy-2-(2-oxo-3-phenylamino-2H-pyridin-1-yl)-acetamide, (RS)-N-(4-arbamimidoyl-2-carbamoylmethoxy-benzyl)-2-ethoxy-2-(2-oxo-3-phenylamino-2H-pyridin-1-yl)-acetamide acetate, (RS)-N-(4-carbamimidoyl-benzyl)-2-ethoxy-2-(6-methyl-2-oxo-1,2-dihydro-pyridin-3-yl)-acetamide hydrochloride, and (RS)-N-(4-carbamimidoyl-benzyl)-2-ethoxy-2-(2-oxo-6-phenyl-1,2-dihydro-pyridin-3-yl)-acetamide hydrochloride, (RS)-N-(4-carbamimidoyl-benzyl)-2-ethoxy-2-(4-fluoro-1,3-dioxo-1,3-dihydro-isoindol-2-yl)-acetamide acetate, (RS)-N-(4-carbamimidoyl-benzyl)-2-ethoxy-2-(5-methyl-1,3-dioxo-1,3-dihydro-isoindol-2-yl)-acetamide, (RS)-N-(4-carbamimidoyl-benzyl)-2-ethoxy-2-(4-methyl-1,3-dioxo-1,3-dihydro-isoindol-2-yl)-acetamide, (RS)-N-(4-carbamimidoyl-benzyl)-2-(4,7-difluoro-1,3-dioxo-1,3-dihydro-isoindol-2-yl)-2-ethoxy-acetamide acetate, (RS)-2-(5-tert-butyl-1,3-dioxo-1,3-dihydro-isoindol-2-yl)-N-(4-carbamimidoyl-benzyl)-2-ethoxy-acetamide, (RS)-N-(4-carbamimidoyl-benzyl)-2-ethoxy-2-(6-methyl-1-oxo-1,3-dihydro-isoindol-2-yl)-acetamide acetate, (RS)-N-(4-carbamimidoyl-benzyl)-2-ethoxy-2-(5-methyl-1-oxo-1,3-dihydro-isoindol-2-yl)-acetamide acetate, (RS)-N-(4-carbamimidoyl-benzyl)-2-ethoxy-2-(4-fluoro-1-oxo-1,3-dihydro-isoindol-2-yl)-acetamide acetate, (RS)-N-(4-carbamimidoyl-benzyl)-2-(4,7-difluoro-1-oxo-1,3-dihydro-isoindol-2-yl)-2-ethoxy-acetamide acetate, (RS)-N-(4-carbamimidoyl-benzyl)-2-ethoxy-2-(4-methyl-1-oxo-1,3-dihydro-isoindol-2-yl)-acetamide acetate, (RS)-N-(4-carbamimidoyl-benzyl)-2-ethoxy-2-(7-methyl-1-oxo-1,3-dihydro-isoindol-2-yl)-acetamide acetate, (RS)-N-[4-carbamimidoyl-2-(2-fluoro-benzylamino)-benzyl]-2-ethoxy-2-(4-methyl-1-oxo-13-dihydro-isoindol-2-yl)-acetamide acetate, (RS)-N-[4-carbamimidoyl-2-(2-fluoro-benzylamino)-benzyl]-2-ethoxy-2-(7-methyl-1-oxo-1,3-dihydro-isoindol-2-yl)-acetamide acetate, (RS)-N-[4-carbamimidoyl-2-(2-fluoro-benzylamino)-benzyl]-2-ethoxy-2-(4-fluoro-1-oxo-1,3-dihydro-isoindol-2-yl)-acetamide acetate, (RS)-N-(4-carbamimidoyl-2-ethylamino-benzyl)-2-ethoxy-2-(4-fluoro-1-oxo-1,3-dihydro-isoindol-2-yl)-acetamide acetate, (RS)-4-[(5-carbamimidoyl-2-{[2-(4-fluoro-1-oxo-1,3-dihydro-isoindol-2-yl)-2-methoxy-acetylamino]-methyl}-phenylamino)-methyl]-benzoic acid methyl ester acetate, (RS)-N-(4-carbamimidoyl-2-ethylamino-benzyl)-2-ethoxy-2-(4-methyl-1-oxo-1,3-dihydro-isoindol-2-yl)-acetamide acetate, (RS)-N-[4-carbamimidoyl-2-(2-fluoro-benzylamino)-benzyl]-2-(6-chloro-1-oxo-1,3-dihydro-isoindol-2-yl)-2-ethoxy-acetamide acetate, (RS)-N-(4-carbamimidoyl-2-ethylamino-benzyl)-2-(6-chloro-1-oxo-1,3-dihydro-isoindol-2-yl)-2-ethoxy-acetamide acetate, (RS)-N-(4-carbamimidoyl-2-ethylamino-benzyl)-2-ethoxy-2-(5-methoxy-1-oxo-1,3-dihydro-isoindol-2-yl)-acetamide acetate, (RS)-N-(2-amino-4-carbamimidoyl-benzyl)-2-ethoxy-2-(5-methoxy-1-oxo-1,3-dihydro-isoindol-2-yl)-acetamide acetate, (RS)-N-(4-carbamimidoyl-2-ethylamino-benzyl)-2-ethoxy-2-(1-oxo-6-piperidin-1-yl-1,3-dihydro-isoindol-2-yl)-acetamide acetate, (RS)-N-[4-carbamimidoyl-2-(2-fluoro-benzylamino)-benzyl]-2-ethoxy-2-(1-oxo-6-piperidin-1-yl-1,3-dihydro-isoindol-2-yl)-acetamide acetate, (RS)-N-(4-carbamimidoyl-2-ethylamino-benzyl)-2-ethoxy-2-(1-oxo-6-pyrrolidin-1-yl-1,3-dihydro-isoindol-2-yl)-acetamide hydrochloride, (RS)-N-[4-carbamimidoyl-2-(2-fluoro-benzylamino)-benzyl]-2-ethoxy-2-(1-oxo-6-pyrrolidin-1-yl-1,3-dihydro-isoindol-2-yl)-acetamide acetate, (RS)-N-[4-carbamimidoyl-2-(2-fluoro-benzylamino)-benzyl]-2-ethoxy-2-(4-fluoro-1,3-dioxo-1,3-dihydro-isoindol-2-yl)-acetamide acetate, (RS)-N-[4-carbamimidoyl-2-(2-fluoro-benzylamino)-benzyl]-2-ethoxy-2-(5-methyl-1,3-dioxo-1,3-dihydro-isoindol-2-yl)-acetamide acetate, (RS)-4-[(5-carbamimidoyl-2-{[2-ethoxy-2-(5-methyl-1,3-dioxo-1,3-dihydro-isoindol-2-yl)-acetylamino]-methyl}-phenylamino)-methyl]-benzoic acid methyl ester acetate, (RS)-N-(4-carbamimidoyl-2-carbamoylmethoxy-benzyl)-2-ethoxy-2-(4-methyl-1-oxo-1,3-dihydro-isoindol-2-yl)-acetamide acetate, (RS)-N-(4-carbamimidoyl-2-carbamoyl methoxy-benzyl)-2-ethoxy-2-(5-methoxy-1-oxo-1,3-dihydro-isoindol-2-yl)-acetamide acetate, (RS)-N-(4-carbamimidoyl-2-methylcarbamoylmethoxy-benzyl)-2-ethoxy-2-(5-methoxy-1-oxo-1,3-dihydro-isoindol-2-yl)-acetamide acetate, (RS)-N-(4-carbamimidoyl-benzyl)-2-ethoxy-2-(3-phenyl-[1,2,4]oxadiazol-5-yl)-acetamide dihydrochloride, and pharmaceutically acceptable salts thereof.

Particularly preferred compounds of formula (I) are those selected from the group consisting of (RS)-N-(4-carbamimidoyl-benzyl)-2-[3-(5-chloro-2-hydroxy-phenyl)-pyrazol-1-yl]-2-ethoxy-acetamide hydrochloride, (RS)-N-(4-carbamimidoyl-benzyl)-2-ethoxy-2-(3-pyridin-4-yl-pyrazol-1-yl)-acetamide acetate, (RS)-N-(4-carbamimidoyl-benzyl)-2-ethoxy-2-(3-phenyl-[1,2,4]triazol-1-yl)-acetamide acetate, (RS)-N-(4-carbamimidoyl-benzyl)-2-[3-(2-hydroxy-phenyl)-4-methyl-pyrazol-1-yl]-acetamide acetate, (RS)-N-(4-carbamimidoyl-benzyl)-2-(1,3-dioxo-1,3-dihydro-isoindol-2-yl)-2-ethoxy-acetamide acetate, (RS)-N-(4-carbamimidoyl-benzyl)-2-ethoxy-2-(2-oxo-3-phenylmethanesulfonylamino-2H-pyridin-1-yl)-acetamide acetate, (RS)-{amino-[4-({2-ethoxy-2-[2-oxo-3-(pyridin-3-ylamino)-2H-pyridin-1-yl]-acetylamino}-methyl)-phenyl]-methylene}-carbamic acid benzyl ester, (RS)-2-ethoxy-N-[2-fluoro-4-(N-hydroxycarbamimidoyl)-benzyl]-2-(2-oxo-3-phenylamino-2H-pyridin-1-yl)-acetamide, (RS)-N-(4-carbamimidoyl-2-carbamoylmethoxy-benzyl)-2-ethoxy-2-(2-oxo-3-phenylamino-2H-pyridin-1-yl)-acetamide acetate, and (RS)-N-(4-carbamimidoyl-benzyl)-2-ethoxy-2-(2-oxo-6-phenyl-1,2-dihydro-pyridin-3-yl)-acetamide hydrochloride, and pharmaceutically acceptable salts thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises converting the nitrile group in a compound of formula (II)

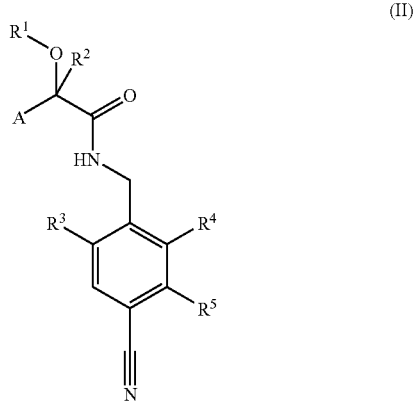

wherein $R^1$, $R^2$, $R^3$, $R^4$, $R^5$ and A have the significances given above, into a carbamimidoyl group, or into a N-hydroxy-carbamimidoyl group, or which process comprises coupling a compound of formula (III) with a compound of formula (IV)

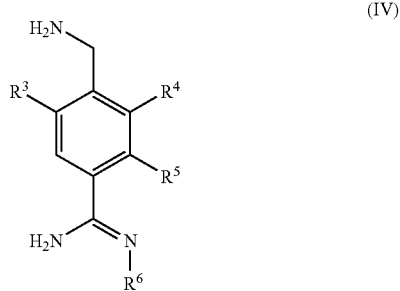

wherein $R^1$, $R^2$, $R^3$, $R^4$, $R^5$, $R^6$ and A have the significances given above, and, if desired, converting an obtained compound of formula (I) into a pharmaceutically acceptable salt.

A preferred process as described above comprises the conversion of the. nitrile group into a carbamamidoyl group, or into a N-hydroxy-carbamimidoyl group.

The conversion of the nitrile group in a compound of formula II into a carbamimidoyl group —C(NH)NH$_2$ or into a N-hydroxy-carbamimidoyl group —C(NOH)NH$_2$ can be carried out according to methods known per se. For example, the conversion into a N-hydroxy-carbamimidoyl group can be performed by dissolving a compound of formula II in a solvent, such as DMF, ethanol or methanol, treating the solution with hydroxylamine or a salt of hydroxylamine with an inorganic acid, such as hydroxylamine hydrochloride, and thereafter with a base, such as diisopropylethylamine or triethylamine, sodium hydride or sodium methanolate, conveniently at a temperature up to 80° C.

The conversion of the nitrile group into a carbamimidoyl group can be carried out e.g. by treating a compound of formula II in a solvent, such as ethanol or methanol, or a solvent mixture, such as chloroform and methanol or chloroform and ethanol, with a dry stream of hydrogen chloride, conveniently at a temperature below 10° C. The solution containing the iminoether can be evaporated and the residue can be treated with gaseous ammonia or an ammonium salt in methanol or ethanol. In so doing, other reactive groups present in the compound of formula I and reactive towards the treatment with hydrogen chloride or gaseous ammonia or ammonium chloride or hydroxylamine can be modified. For example, in the case of treatment with hydrogen chloride a benzyloxy group can be converted into the hydroxy group. In the case of treatment with gaseous ammonia in methanol or ethanol a lower-alkoxy-carbonyl-lower-alkoxy group can be converted into a carbamoyl-lower-alkoxy group.

A compound of formula (I) can further be obtained by coupling a compound of formula (III) with a compound of formula (IV). The coupling of compounds of formula (III) with compounds of formula (IV) can be carried out by general methods for coupling acids with amines well known in the art, e.g. by coupling in the presence of coupling reagents such as BOP or EDCl/HOBt and a organic base such as triethylamine or diisopropyl ethyl amine in solvents such as THF or DMF.

If a carbamimidoyl compound of formula (I) is obtained from a nitrile of formula (II) by treatment with hydrogen chloride and subsequent reaction with gaseous ammonia or ammonium chloride, the carbamimidoyl product is obtained as hydrochloride salt. This salt can be converted into any other pharmaceutically acceptable salt by chromatography over an adequately charged basic ion exchange resin. Alternatively the hydrochloride salt of a carbamimidoyl compound of formula (I) can be converted into the corresponding free base by treatment with sodium ethanolate in ethanol and subsequently treated with an excess of an appropriate acid to generate any pharmaceutically acceptable salt.

Any pharmaceutically acceptable salt of a carbamimidoyl compound of formula (I) can furthermore be obtained when a N-hydroxy-carbamimidoyl compound of formula (I) is hydrogenated in a solvent like ethanol, methanol, dioxan or THF, with hydrogen and a catalyst such as palladium, platinum or nickel in the presence of an appropriate acid.

Functional groups in compounds of formula (I) can be modified. As modifications of functional groups in a compound of formula I there come into consideration especially the conversion of a N-hydroxy-carbamimidoyl group into a carbamimidoyl group, the esterification of a carboxy group, the saponification of an ester group and the cleavage of an ether group, such as an arylalkyl ether group, e.g. the benzyl ether group. All of these reactions can be carried out according to methods known per se.

A compound of formula (I) in which $R^6$ represents a hydroxy group can be converted into a compound of formula (I) in which $R^6$ represents hydrogen by hydrogenation in a solvent, such as ethanol, methanol, dioxane, THF or glacial acetic acid, or a solvent mixture, such as ethanol and glacial acetic acid, with hydrogen and a catalyst, such as palladium, platinum or nickel. In so doing, other reactive groups present in the compound of formula I and reactive towards the reducing agent can be modified.

A compound of formula (I) in which $R^6$ represents benzyloxy-carbonyl can be converted into a compound of formula (I) in which $R^6$ represents hydrogen by hydrogenation in a solvent, such as ethanol, methanol, dioxane, THF or glacial acetic acid, or a solvent mixture, such as ethanol and glacial acetic acid, with hydrogen and a catalyst, such as palladium. The reaction can be optionally performed in the presence of an acid such as HCl in a solvent such as EtOH or MeOH. In so doing, other reactive groups present in the compound of formula I and reactive towards the reducing agent can be modified.

A compound of formula (I) in which $R^6$ represents lower-alkoxy-carbonyl or aryl-lower-alkoxy-carbonyl is obtained by reacting a compound of formula (I) in which $R^6$ represents hydrogen with a chloroformic acid lower alkyl ester or a chloroformic acid aryl-lower-alkyl ester in a solvent, such as dichloromethane, dioxane or DMF, or a solvent mixture, such as dichloromethane and water or ethyl acetate and water, in the presence of an organic base, such as pyridine or triethylamine, or an inorganic base, such as sodium hydroxide, sodium carbonate or potassium bicarbonate.

A compound of formula (I) in which $R^6$ represents benzyloxy-carbonyl can be prepared according to general methods known per se, e.g. by coupling of an acid of formula IIIa or IIIb and [(4-aminomethyl-phenyl)-imino-methyl]-carbamic acid benzyl ester dihydrochloride in the presence of coupling reagents as BOP or EDCl/HOBt and a organic base such as triethylamine or diisopropyl ethyl amine in a solvent such as THF.

A compound of formula (I) in which $R^6$ represents lower-alkyl-carbonyl or aryl-carbonyl is obtained by reacting a compound of formula (I) in which $R^6$ represents hydrogen with a acyl chloride in a solvent, such as dichloromethane, dioxane or DMF, or a solvent mixture, such as dichloromethane and water or ethyl acetate and water, in the presence of an organic base, such as pyridine or triethylamine, or an inorganic base, such as sodium hydroxide, sodium carbonate or potassium bicarbonate.

A compound of formula (II) in which a phenolic hydroxy group is present can be reacted with an alkylating agent such as an appropriately substituted alkyl bromide, alkyl iodide or alkyl mesylate in the presence of a base such as potassium carbonate or caesium carbonate in a solvent such as DMF or acetone.

A compound of formula (II) in which an aniline group is present can be reacted with an acyl or a sulfonyl chloride or a chloroformic acid ester in the presence of an organic base such as triethyl amine or diisopropyl ethyl amine in a solvent such as DMF, THF or acetonitrile.

The compounds of formula (II) are prepared according to general methods known per se, e.g. by coupling of an acid of formula (IIIa) or of formula (IIIb) and an appropriately substituted 4-aminomethyl benzonitrile (VII) in the presence of coupling reagents such as BOP or EDCl/HOBt and an organic base such as triethylamine or diisopropyl ethyl amine in solvents such as THF or DMS.

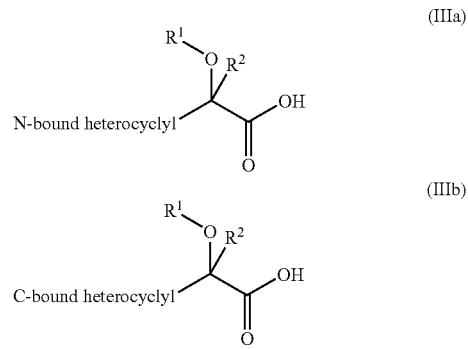

Compounds of formula (IIIa) are known per se or can be prepared according to general methods known per se, e.g. as described hereinafter and/or as described in the Examples or in analogy to these methods.

For example, a compound of formula (IIIa) can be prepared by alkylation of a nitrogen-containing heterocycle (V) with 2-chloro-2-ethoxy acetic acid ethyl ester in DMF as solvent using potassium tert-butylate or sodium hydride as base, and subsequent hydrolysis of the ester.

Compounds of formula (V) are known per se or can be prepared according to general methods known per se, e.g. as described hereinafter and/or as described in the Examples or in analogy to these methods.

A compound of formula (IIIb) can for example be prepared by reaction of an aldehyde of formula (VI) with bromoform or chloroform in a mixture of solvents like dioxane/methanol or dioxane/ethanol in the presence of an inorganic base like sodium hydroxide or potassium hydroxide, or by reaction of an aldehyde of formula (VI) with trimethylsilyl cyanide in the presence of $ZnI_2$ in a solvent such as dichloromethane. The trimethylsilyl cyanohydrine thus obtained is subsequently hydrolysed in concentrated hydrochloric acid to the corresponding a-hydroxy carboxylic acid which is then alkylated to give a compound of formula (IIIb) using an appropiately substituted alkyl halide in the presence of silver oxide in a solvent such as toluene.

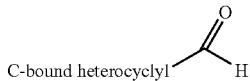
(VI)

Compounds of formula (VI) are known per se or can be prepared according to general methods known in the art, e.g. as described hereinafter and/or as described in the examples or in analogy to these methods.

Compounds of formula (VII) can be prepared according to general methods known in the art, e.g as described hereinafter and/or as described in the examples or in analogy to these.

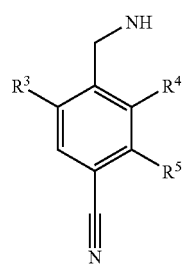
(VII)

A compound of formula (II) where A is a 1,2,4-oxadiazol-5-yl ring and R2 is H can be prepared from a compound of formula (VIII) by saponification with a base such as LiOH in a solvent mixture such as THF/MeOH/H₂O and subsequent reaction with a compound of formula (IX) in the presence of a coupling reagent such as 1,1'-carbonyl diimidazole in a solvent such as THF followed by heating of the intermediate product with microwave radiation in a solvent such as DMF.

A compound of formula (VIII) can be prepared by reaction of a compound of formula (VII) and a compound of formula (X) in the presence of a coupling reagent such as BOP and an organic base such as diisopropyl ethyl amine in a solvent such as THF.

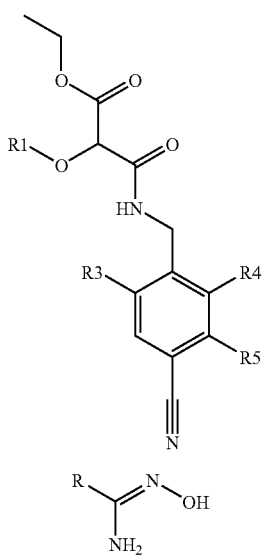
(VIII)

(IX)

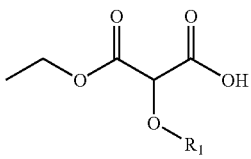
(X)

Compounds of formula (I) as described above, wherein R⁵ and R⁶ are bound together to form a ring and —R⁵—R⁶— is —O— or —NH—, can be obtained by coupling a compound of formula (III) with an appropriate compound of formula (IV) wherein R⁵ and R⁶ are bound together. Appropriate starting materials of formula (IV) are known in the art or can be prepared by methods known in the art or described herein or by analogous methods.

Insofar as their preparation is not described in the examples, the compounds, intermediates and starting materials referred to above can be prepared according to analogous methods or according to the methods set forth above.

A compound of formula (IIIb) can for example be prepared by reaction of an aldehyde of formula (VI) with bromoform or chloroform in a mixture of solvents like dioxane/methanol or dioxane/ethanol in the presence of an inorganic base like sodium hydroxide or potassium hydroxide, or by reaction of an aldehyde of formula (VI) with trimethylsilyl cyanide in the presence of ZnI₂ in a solvent such as dichloromethane. The trimethylsilyl cyanohydrine thus obtained is subsequently hydrolysed in concentrated hydrochloric acid to the corresponding □-hydroxy carboxylic acid which is then alkylated to give a compound of formula (IIIb) using an appropiately substituted alkyl halide in the presence of silver oxide in a solvent such as toluene.

(VI)

Compounds of formula (VI) are known per se or can be prepared according to general methods known in the art, e.g. as described hereinafter and/or as described in the examples or in analogy to these methods.

Compounds of formula (VII) can be prepared according to general methods known in the art, e.g as described hereinafter and/or as described in the examples or in analogy to these.

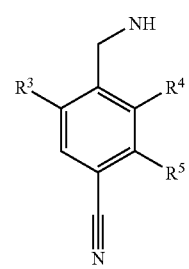
(VII)

Compounds of formula (I) as described above, wherein R⁵ and R⁶ are bound together to form a ring and —R⁵—R⁶— is —O— or —NH—, can be obtained by coupling a compound of formula (III) with an appropriate compound of formula (IV) wherein $R^5$ and $R^6$ are bound together. Appropriate starting materials of formula (IV) are known in the art or can be prepared by methods known in the art or described herein or by analogous methods.

Insofar as their preparation is not described in the examples, the compounds, intermediates and starting materials referred to above can be prepared according to analogous methods or according to the methods set forth above.

Furthermore, the invention relates to compounds of formula (I) as defined above, when manufactured by a process as described above. In another embodiment, the invention relates to the intermediates, the compounds of formula (I)

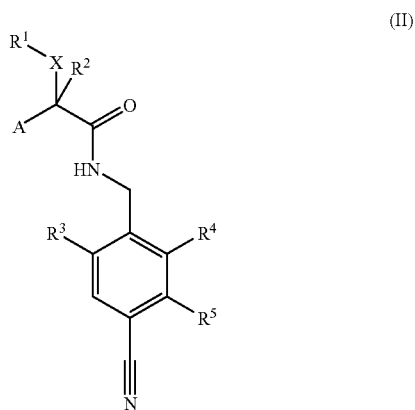

(II)

wherein $R^1$, $R^2$, $R^3$, $R^4$, $R^5$ and A have the significances given above.

As described above, the compounds of formula (I) are active compounds and inhibit the formation of coagulation factors Xa, IXa and thrombin induced by factor VIIa and tissue factor or are derivatives which are converted under physiological conditions to such active compounds. These compounds consequently influence both platelet aggregation which is induced by these factors and plasmatic blood coagulation. They therefore inhibit the formation of thrombi and can be used for the treatment and/or prevention of diseases, such as arterial and venous thrombosis, deep vein thrombosis, pulmonary embolism, unstable angina pectoris, cardiac infarction, stroke due to atrial fibrillation, inflammation and arteriosclerosis. Furthermore, these compounds have an effect on tumour cells and prevent metastases. They can therefore also be used as antitumour agents. Prevention and/or treatment thrombosis, particularly arterial or deep vein thrombosis, is the preferred indication.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are associated with the formation of clotting factors Xa, IXa and thrombin induced by factor VIIa and tissue factor, particularly as therapeutically active substances for the treatment and/or prophylaxis of arterial and venous thrombosis, deep vein thrombosis, pulmonary embolism, unstable angina pectoris, cardiac infarction, stroke due to atrial fibrillation, inflammation, arteriosclerosis and/or tumour.

In another preferred embodiment, the invention relates to a method for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumour, which method comprises administering a compound as defined above to a human being or animal.

The invention also embraces the use of compounds as defined above for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumour.

The invention also relates to the use of compounds as described above for the preparation of medicaments for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumour. Such medicaments comprise a compound as described above.

The inhibition of the amidolytic activity of factor VIIa/tissue factor complex by the compounds in accordance with the invention can be demonstrated with the aid of a chromogenic peptide substrate as described hereinafter.

The measurements were carried out by an automated robotic assay on microtitre plates at room temperature. To this end, 100 μl of a solution of 26 nM of tissue factor, 9 nM of soluble factor VIIa and 8 mM of calcium chloride were added to 25 μl of a solution of the inhibitor in a buffer [pH 7.5, 100 mM, comprising 0.14M NaCl, 0.1M N-(2-hydroxyethyl)piperazine-N'-(2-ethanesulphonic acid) (HEPES), 0.5 mg/l of fatty-acid-free BSA (bovine serum albumin) and 0.05% NaN$_3$] in each well of the plate. After an incubation time of 15 minutes the reaction was started by the addition of 50 μl of chromogenic substrate Chromozym-tPA (3.5 mM, MeSO$_2$-D-Phe-Gly-Arg-paranitroanilide) and the hydrolysis of the substrate was followed spectrophotometrically on a kinetic microtitre plate reader over 10 minutes. Using the plot of the inhibition curves, the Ki values were determined according to the method described in Biochem. J. 55, 1953, 170–171.

The activity of the compounds of the present invention can, moreover, be characterized in the "prothrombin time" (PT) clotting test. The substances are prepared as a 10 mM solution in DMSO or DMSO/0.1M HCl (DHCl) and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 μl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 μl of plasma/inhibitor mixture in the measurement container. The clotting reaction was initiated by the addition of 0.1 ml of Innovin® (recombinant human tissue factor combined with calcium buffer and synthetic phospholipids(Dade Behring®, Inc.). The time up to the fibrin cross-linking was determined photooptically from the ACL. The inhibitor concentration, which brought about a doubling of the PT clotting time, was determined by means of a graph.

The Ki value of the active compounds of the present invention preferably amounts to about 0.001 to 50 μM, especially about 0.001 to 1 μM. The PT values preferably amount to about 1 to 100 μM, especially to about 1 to 10 μM.

| Example | Ki [μM] |
|---------|---------|
| 4.3     | 0.76    |
| 10.4    | 1.41    |
| 13.4    | 1.08    |
| 19.5    | 0.43    |
| 27      | 0.46    |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules).

Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

Abbreviations

BOP=(benzotriazol-1-yloxy)-tris-(dimethylamino)-phosphonium-hexafluorophosphat, CAS=Chemical Abstract Services, DEAD=diethyl azodicarboxylate, DMF=dimethyl formamide, EDCl=1-[3-(dimethylamino)propyl]-3-ethyl-carbodiimide hydrochloride, EtOAc=ethyl acetate, EtOH=ethanol, HOBT=1-hydroxybenzotriazole, MS=mass spectroscopy, MeOH=methanol, r.t.=room temperature, THF=tetrahydrofuran General Procedures General Procedure A: N-Alkylation of Pyrazoles or Triazoles with 2-chloro-2-ethoxyacetic Acid Ethyl Ester To a stirred, cooled (0° C.) solution of the starting nitrogen-containing heterocycle (pyrazole or triazole) in DMF under argon was added portionwise potassium tert-butylate (1 eq) and stirring at 0° C. was continued for 1 h. A DMF solution of 2-chloro-2-ethoxyacetic acid ethyl ester (1 eq) was then added and stirring was continued for 2–8 hrs. Water was added to the mixture and the product was extracted with EtOAc. The combined organics were washed with water and brine, dried (MgSO4), filtered and concentrated. The crude product was isolated by column chromatography (silica gel).

General Procedure B: Hydrolysis of heteroaryl-α-alkoxyacetic Acid Esters

Solid NaOH (3 eq) was added to a stirred solution of the starting ester at r.t. in of ethanol/water 1:1. After stirring for 1–8 h, the mixture was concentrated to leave a white solid. This residue was dissolved in water and the resulting solution was washed with EtOAc. The aqueous phase was acidified to pH~1 by the dropwise addition of 1.0 N HCl. The product was then extracted with EtOAc. The combined organics were washed with brine, dried (MgSO4), filtered and concentrated to leave the crude product as a white solid which was usually used without further purification.

General Procedure C: Coupling of an aryl-α-alkoxyacetic Acid with a Primary Amine using BOP as a Coupling Reagent To a stirred solution of the amine (1 eq) in THF is added the acid (1.5 eq), N-diisopropylamine (1.5 eq) and BOP-reagent (1.5 eq). The mixture is then stirred at r.t. under an argon atmosphere for 16–24 h. The mixture is diluted with EtOAc, washed with water, 1.0 N NaOH and brine; dried (MgSO$_4$), filtered and concentrated. The crude product can be purified by chromatography (silica gel) or by crystallization.

General Procedure D: Conversion of an Aromatic Nitrile into an Amidine (Pinner Reaction)

Dry HCl gas is passed over a cooled (−10° C.), stirred solution of the starting material in $CHCl_3$/EtOH (or MeOH) 5:1 for 15 min. The flask is stoppered and left at 4° C. overnight. If conversion is not complete, the reaction mixture is allowed to warm to r.t. The mixture is concentrated (rotavapor and high vacuum) at r.t. The residue is dissolved in EtOH and treated with a 2.0 M $NH_3$ solution in EtOH. The resulting mixture is stirred at r.t. (sensitive compounds) or 60° C. for 2–18 h. The mixture is then concentrated (rotavapor) and purified by chromatography (silica gel).

General Procedure E: Hydrogenolysis of a Benzyloxycarbonyl-Protected Amidine

To a stirred suspension of the palladium catalyst (10 w %) in ethanol under an argon atmosphere were added a few drops of acetic acid and the starting material. The mixture was then stirred at r.t. under a hydrogen atmosphere for 18 h. The catalyst was filtered over a celite pad and the cake was washed with ethanol. The filtrate was concentrated. The product was isolated by precipitation with EtOAc/$CH_2Cl_2$ or by chromatography (silica gel).

General Procedure F: Conversion of a Nitrile into an Amidoxime

To a stirred solution of the starting material at r.t. in ethanol under an argon atmosphere were added triethylamine (5 eq) and hydroxylamine hydrochloride (5 eq). Stirring was continued for 18 hrs. The mixture was concentrated. The crude product was isolated by chromatography (silica gel).

General Procedure G: Conversion of an Amidoxime into an Amidine

To a stirred suspension of a catalytic amount of Raney nickel in ethanol at r.t. under an argon atmosphere were added a few drops of acetic acid and the starting material. Stirring under a hydrogen atmosphere was continued for 6–24 hrs. The catalyst was filtered off and the filtrate was concentrated to leave the product as a solid. If necessary the product was purified by column chromatography (silica gel).

General Procedure H: N-Alkylation of 1-oxo-1,3-dihydro-isoindoles or 1,3-dioxo-1,3-dihydro-isoindoles with 2-chloro-2-ethoxyacetic Acid Ethyl Ester To a stirred, cooled (0° C.) solution of the starting nitrogen-containing heterocycle (1-oxo-1,3-dihydro-isoindole or 1,3-dioxo-1,3-dihydro-isoindole) in DMF under argon was added sodium hydride (1 eq as 50% dispersion in mineral oil) and stirring was continued at ambient temperature until evolution of $H_2$ had ceased. 2-Chloro-2-ethoxy-acetic acid ethyl ester (1.05 eq), dissolved in a tiny amount of DMF, was then added at 0° C. and stirring was continued for typically 30 Min. Water and $NH_4Cl$-solution was carefully added to the reaction mixture and the product was extracted with EtOAc. The combined organic layers were washed with water, dried ($MgSO_4$), filtered and concentrated. Finally, the product was isolated by column chromatography (silica gel, hexane/AcOEt).

Example 1

1.1

3-(4-Methoxyphenyl)pyrazole (CAS 27069-17-6) was reacted with 2-chloro-2-ethoxy-acetic acid ethyl ester according to general procedure A to give (RS)-ethoxy-[3-(4-methoxy-phenyl)-pyrazol-1-yl]-acetic acid ethyl ester. Colorless oil. MS 305.1 ($[M+H]^+$)

1.2

(RS)-Ethoxy-[3-(4-methoxy-phenyl)-pyrazol-1-yl]-acetic acid ethyl ester was hydrolysed according to general procedure B to give (RS)-ethoxy-[3-(4-methoxy-phenyl)-pyrazol-1-yl]-acetic acid. White solid. MS 275.1 ($[M-H]^-$)

1.3

(RS)-Ethoxy-[3-(4-methoxy-phenyl)-pyrazol-1-yl]-acetic acid was coupled with 4-aminomethyl benzonitrile according to general procedure C to give (RS)-N-(4-cyano-benzyl)-2-ethoxy-2-[3-(4-methoxy-phenyl)-pyrazol-1-yl]-acetamide. White amorphous solid. MS 391.2 ($[M+H]^+$)

1.4

(RS)-N-(4-Cyano-benzyl)-2-ethoxy-2-[3-(4-methoxy-phenyl)-pyrazol-1-yl]-acetamide was converted to (RS)-N-(4-carbamimidoyl-benzyl)-2-ethoxy-2-[3-(4-methoxy-phenyl)-pyrazol-1-yl]-acetamide hydrochloride according to general procedure D. White solid. MS 408.3 ($[M+H]^+$)

Example 2

In analogy to example 1,3-phenylpyrazole (CAS 2458-26-6) was converted to (RS)-N-(4-carbamimidoyl-benzyl)-2-ethoxy-2-(3-phenyl-pyrazol-1-yl)-acetamide hydrochloride. White solid. MS 378.3 ($[M+H]^+$).

Example 3

In analogy to example 1,3'-(5-methyl-1H-pyrazol-3-yl)-pyridine (CAS 19959-72-9) was converted to (RS)-N-(4-carbamimidoyl-benzyl)-2-ethoxy-2-(5-methyl-3-pyridin-3-yl-pyrazol-1-yl)-acetamide acetate. MS 393.2 ($[M+H]^+$)

Example 4

4.1

To a stirred solution of 4-chloro-2-(1H-pyrazol-3-yl)-phenol (1 g, CAS 18704-67-1) at r.t. in acetone (20 ml) under an argon atmosphere were added $K_2CO_3$ (746 mg) and benzylbromid (0.61 ml). The reaction mixture was stirred at r.t. for 21 h. The solids were filtered off and washed with acetone. The filtrate was concentrated to leave a light orange oil. The crude product was purified by chromatography (silica gel, cyclohexane/ethyl acetate 2:1) to give 3-(2-benzyloxy-5-chloro-phenyl)-1H-pyrazole as off-white solid. MS 284.8 ($[M+H]^+$)

4.2

Using analogous procedures as described in example 1,3-(2-benzyloxy-5-chloro-phenyl)-1H-pyrazole was converted to (RS)-2-[3-(2-benzyloxy-5-chloro-phenyl)-pyrazol-1-yl]-N-(4-carbamimidoyl-benzyl)-2-ethoxy-acetamide hydrochloride. MS 518.2 ($[M+H]^+$)

4.3

To a stirred suspension of 10% Pd/C (10 mg) at r.t. in ethanol (2 ml) was added (RS)-2-[3-(2-benzyloxy-5-chloro-phenyl)-pyrazol-1-yl]-N-(4-carbamimidoyl-benzyl)-2-ethoxy-acetamide hydrochloride (100 mg). Stirring at r.t. under a hydrogen atmosphere was continued for 3 hrs. The catalyst was filtered off over a celite pad and washed with ethanol. The filtrate was concentrated to give (RS)-N-(4-carbamimidoyl-benzyl)-2-[3-(5-chloro-2-hydroxy-phenyl)-pyrazol-1-yl]-2-ethoxy-acetamide hydrochloride (48 mg) as off-white solid. MS 428.2 ($[M+H]^+$)

Example 5

5.1

Using analogous procedures as described in examples 1.1 to 1.3, 3-(3-nitrophenyl)pyrazole (CAS 59843-77-5) was converted to (RS)-N-(4-cyano-benzyl)-2-ethoxy-2-[3-(3-nitro-phenyl)-pyrazol-1-yl]-acetamide. MS 404.2 ([M−H]$^-$)

5.2

To a stirred suspension of 10% Pd/C (214 mg) at r.t. in ethanol (4 ml) under an argon atmosphere was added of (RS)-N-(4-cyano-benzyl)-2-ethoxy-2-[3-(3-nitro-phenyl)-pyrazol-1-yl]-acetamide (2.1 g). The mixture was stirred at r.t. under a hydrogen atmosphere for 18 h. The catalyst was filtered over a celite pad and the cake was washed with ethanol. The filtrate was concentrated. The crude product was purified by chromatography (silica gel, gradient cyclohexane=>EtOAc) to give (RS)-2-[3-(3-amino-phenyl)-pyrazol-1-yl]-N-(4-cyano-benzyl)-2-ethoxy-acetamide (1.0 g) as off-white solid. MS 376.5 ([M+H]$^+$)

5.3

According to general procedure D, (RS)-2-[3-(3-aminophenyl)-pyrazol-1-yl]-N-(4-cyano-benzyl)-2-ethoxy-acetamide was converted to (RS)-2-[3-(3-amino-phenyl)-pyrazol-1-yl]-N-(4-carbamimidoyl-benzyl)-2-ethoxy-acetamide hydrochloride. Off-white solid. MS 393.2 ([M+H]$^+$)

Example 6

6.1

To a stirred, cooled (0° C.) solution of (RS)-2-[3-(3-amino-phenyl)-pyrazol-1-yl]-N-(4-cyano-benzyl)-2-ethoxy-acetamide (117 mg, example 5.2) in dichloromethane (5 ml) under an argon atmosphere were added triethylamine (0.06 ml) and acetyl chloride (0.02 ml). Stirring at 0° C. was continued for 3 hrs. The mixture was diluted with EtOAc, washed with 1.0 N HCl and brine, dried (MgSO$_4$), filtered and concentrated. The crude product was isolated by chromatography (silica gel, gradient CH$_2$Cl$_2$ to CH$_2$Cl$_2$/MeOH 9:1) to give 2-[3-(3-acetylamino-phenyl)-pyrazol-1-yl]-N-(4-cyano-benzyl)-2-ethoxy-acetamide (115 mg) as off-white solid. MS 418.2 ([M+H]$^+$)

6.2

According to general method D, 2-[3-(3-acetylaminophenyl)-pyrazol-1-yl]-N-(4-cyano-benzyl)-2-ethoxy-acetamide1 was converted to (RS)-2-[3-(3-acetylamino-phenyl)-pyrazol-1-yl]-N-(4-carbamimidoyl-benzyl)-2-ethoxy-acetamide hydrochloride. Off-white solid. MS 435.3 ([M+H]$^+$)

Example 7

Using similar procedures as described in example 6, (RS)-2-[3-(3-amino-phenyl)-pyrazol-1-yl]-N-(4-cyano-benzyl)-2-ethoxy-acetamide (example 5.2) was converted to (RS)-N-(4-carbamimidoyl-benzyl)-2-ethoxy-2-[3-(3-methanesulfonylamino-phenyl)-pyrazol-1-yl]-acetamide hydrochloride. Off-white solid. MS 469.3 ([M+H]$^+$)

Example 8

8.1

Using analogous procedures as described in examples 1.1 and 1.2, 4-(1H-pyrazol-3-yl)-pyridine (CAS 17784-60-0) was converted to ethoxy-(3-pyridin-4-yl-pyrazol-1-yl)-acetic acid. Light yellow solid. MS 246.3 ([M−H]$^-$)

8.2

According to general method C, ethoxy-(3-pyridin-4-yl-pyrazol-1-yl)-acetic acid was reacted with [(4-aminomethyl-phenyl)-imino-methyl]-carbamic acid benzyl ester dihydrochloride (CAS 172348-75-3) to give (RS)-[amino-(4-{[2-ethoxy-2-(3-pyridin-4-yl-pyrazol-1-yl)-acetylamino]-methyl}-phenyl)-methylene]-carbamic acid benzyl ester. White powder. MS 513.3 ([M+H]$^+$)

8.3

According to general method E, (RS)-[amino-(4-{[2-ethoxy-2-(3-pyridin-4-yl-pyrazol-1-yl)-acetylamino]-methyl}-phenyl)-methylene]-carbamic acid benzyl ester was converted to (RS)-N-(4-carbamimidoyl-benzyl)-2-ethoxy-2-(3-pyridin-4-yl-pyrazol-1-yl)-acetamide acetate. Off-white powder. MS 379.3 ([M+H]$^+$)

Example 9

9.1

Using analogous procedures as described in example 1.1 to 1.3, 3-phenyl-1H-[1,2,4]triazole (CAS 3357-42-4) was converted to (RS)-N-(4-cyano-benzyl)-2-ethoxy-2-(3-phenyl-[1,2,4]triazol-1-yl)-acetamide. White amorphous solid. MS 362.2 ([M+H]$^+$)

9.2

According to general procedure F, (RS)-N-(4-cyano-benzyl)-2-ethoxy-2-(3-phenyl-[1,2,4]triazol-1-yl)-acetamide was converted to (RS)-2-ethoxy-N-[4-(N-hydroxycarbamimidoyl)-benzyl]-2-(3-phenyl-[1,2,4]triazol-1-yl)-acetamide. White solid. MS 395.1 ([M+H]$^+$)

9.3

According to general procedure G, (RS)-2-ethoxy-N-[4-(N-hydroxycarbamimidoyl)-benzyl]-2-(3-phenyl-[1,2,4]triazol-1-yl)-acetamide was converted to (RS)-N-(4-carbamimidoyl-benzyl)-2-ethoxy-2-(3-phenyl-[1,2,4]triazol-1-yl)-acetamide acetate. Light yellow solid. MS 379.3 ([M+H]$^+$)

Example 10

10.1

Using a method described in J. Agric. Food Chem. (1977), 25(5), p. 1039, 1-(2-benzyloxy-phenyl)-propan-1-one (CAS 64686-65-3) was converted to 3-(2-benzyloxy-phenyl)-4-methyl-1H-pyrazole. Orange gum. MS 264.2 ([M]$^+$)

10.2

Using analogous methods as described in examples 1.1 to 1.3, 3-(2-benzyloxy-phenyl)-4-methyl-1H-pyrazole was converted to (RS)-2-[3-(2-benzyloxy-phenyl)-4-methyl-pyrazol-1-yl]-N-(4-cyano-benzyl)-2-ethoxy-acetamide. Off-white amorphous solid. MS 481.5 ([M+H]$^+$)

10.3

According to general method F, (RS)-2-[3-(2-benzyloxyphenyl)-4-methyl-pyrazol-1-yl]-N-(4-cyano-benzyl)-2-ethoxy-acetamide was converted to (RS)-2-[ 3-(2-benzyloxy-phenyl)-4-methyl-pyrazol-1-yl]-2-ethoxy-N-[4-(N-hydroxycarbamimidoyl)-benzyl]-acetamid. Off-white solid. MS 512.3 ([M−H]$^-$)

10.4

To a stirred solution of (RS)-2-[3-(2-benzyloxy-phenyl)-4-methyl-pyrazol-1-yl]-2-ethoxy-N-[4-(N-hydroxycarbamimidoyl)-benzyl]-acetamide (90 mg) at r.t. in ethanol were added acetic acid (3 drops) and 10% Pd/C (9 mg). Stirring at r.t. under a hydrogen atmosphere was continued for 18 hrs. The catalyst was filtered off and washed with ethanol. The filtrate was concentrated. The crude product was purified by chromatography (silica gel, EtOAc/acetone/$H_2O$/HOAc 6:2:1:1) to give (RS)-N-(4-carbamimidoyl-benzyl)-2-ethoxy-2-[3-(2-hydroxy-phenyl)-4-methyl-pyrazol-1-yl]-acetamide acetate (28 mg) as off-white solid. MS 408.5 ($[M+H]^+$).

Example 11

11.1

To a stirred suspension of (RS)-2-[3-(2-benzyloxy-phenyl)-4-methyl-pyrazol-1-yl]-N-(4-cyano-benzyl)-2-ethoxy-acetamide (1.2 g, example 10.2) at r.t. in ethanol (20 ml) under an argon atmosphere was added 10% Pd/C (60 mg). The mixture was then stirred under a hydrogen atmosphere for 18 h. The catalyst was filtered off and washed with ethanol. The filtrate was concentrated. The crude product was isolated by chromatography (silica gel, gradient cyclohexane=>cyclohexane/EtOAc 2:3) to give (RS)-N-(4-cyano-benzyl)-2-ethoxy-2-[3-(2-hydroxy-phenyl)-4-methyl-pyrazol-1-yl]-acetamide (428 mg) as white solid. MS 389.5 ($[M-H]^-$)

11.2

To a stirred solution of (RS)-N-(4-cyano-benzyl)-2-ethoxy-2-[3-(2-hydroxy-phenyl)-4-methyl-pyrazol-1-yl]-acetamide (200 mg) at r.t. in DMF (4 ml) under an argon atmosphere were added cesium carbonate (200 mg) followed by iodoacetamide (114 mg). The mixture was then stirred for 2 h. The mixture was diluted with EtOAc and water. The aqueous phase was extracted with EtOAc. The combined organics were washed with water. A solid started to precipitate out of the organic phase in the separating funnel. This solid was collected by filtration and washed with cyclohexane to give (RS)-2-[3-(2-carbamoylmethoxy-phenyl)-4-methyl-pyrazol-1-yl]-N-(4-cyano-benzyl)-2-ethoxy-acetamide (153 mg) as white powder. The organic layer of the filtrate was separated and washed with brine, dried ($MgSO_4$), filtered and concentrated to leave a yellow solid. This was taken in $Et_2O$ (5 ml) and 5 drops of methanol were added. The suspension was stirred for 30 min at r.t. and this second crop of product was collected by filtration, washed with $Et_2O$ and dried to give more (RS)-2-[3-(2-carbamoylmethoxy-phenyl)-4-methyl-pyrazol-1-yl]-N-(4-cyano-benzyl)-2-ethoxy-acetamide (31 mg) of an off-white powder. MS 448.5 ($[M+H]^+$)

11.3

According to general methods F and G, (RS)-2-[3-(2-carbamoylmethoxy-phenyl)-4-methyl-pyrazol-1-yl]-N-(4-cyano-benzyl)-2-ethoxy-acetamide was converted to (RS)-N-(4-carbamimidoyl-benzyl)-2-[3-(2-carbamoylmethoxy-phenyl)-4-methyl-pyrazol-1-yl]-2-ethoxy-acetamide acetate. Off-white solid. MS 465.5 ($[M+H]^+$)

Example 12

12.1

Using an analogous procedure as described in example 11.2 (RS)-N-(4-cyano-benzyl)-2-ethoxy-2-[3-(2-hydroxy-phenyl)-4-methyl-pyrazol-1-yl]-acetamide was reacted with ethyl iodoacetate to give (RS)-(2-{1-[(4-cyano-benzylcarbamoyl)-ethoxy-methyl]-4-methyl-1H-pyrazol-3-yl}-phenoxy)-acetic acid ethyl ester. White amorphous solid. MS 477.5 ($[M+H]^+$)

12.2

According to general method F, (RS)-(2-{1-[(4-cyano-benzylcarbamoyl)-ethoxy-methyl]-4-methyl-1H-pyrazol-3-yl}-phenoxy)-acetic acid ethyl ester was converted to (RS)-[2-(11-{ethoxy-[4-(N-hydroxycarbamimidoyl)-benzylcarbamoyl]-methyl}-4-methyl-1H-pyrazol-3-yl)-phenoxy]-acetic acid ethyl ester. Off-white solid. MS 510.5 ($[M+H]^+$)

12.3

According to general method G, (RS)-[2-(1-{ethoxy-[4-(N-hydroxycarbamimidoyl)-benzylcarbamoyl]-methyl}-4-methyl-1H-pyrazol-3-yl)-phenoxy]-acetic acid ethyl ester was converted to (RS)-(2-{1-[(4-carbamimidoyl-benzylcarbamoyl)-ethoxy-methyl]-4-methyl-1H-pyrazol-3-yl}-phenoxy)-acetic acid ethyl ester acetate. Off-white solid. MS 494.4 ($[M+H]^+$)

12.4

To a stirred mixture of (RS)-(2-{1-[(4-carbamimidoyl-benzylcarbamoyl)-ethoxy-methyl]-4-methyl-1H-pyrazol-3-yl}-phenoxy)-acetic acid ethyl ester acetate (82 mg) at r.t. in ethanol/$H_2O$ 1:1 (2 ml) was added sodium hydroxyde (20 mg). Stirring was then continued for 2 h. The mixture was concentrated to leave an off-white paste. The crude product was isolated by chromatography (silica gel, EtOAc/acetone/$H_2O$/HOAc 6:2:1:1) to give (RS)-(2-{1-[(4-carbamimidoyl-benzylcarbamoyl)-ethoxy-methyl]-4-methyl-1H-pyrazol-3-yl}-phenoxy)-acetic acid acetate (58 mg) as an off-white solid. MS 466.4 ($[M+H]^+$)

Example 13

13.1

According to general procedure A, phthalimide potassium salt was reacted with 2-chloro-2-ethoxyacetic acid ethyl ester dihydrochloride (CAS 172348-75-3) to give (RS)-(1,3-dioxo-1,3-dihydro-isoindol-2-yl)-ethoxy-acetic acid ethyl ester. Light yellow semisolid. MS 278.0 ($[M+H]^+$)

13.2

According to general procedure B, (RS)-(1,3-dioxo-1,3-dihydro-isoindol-2-yl)-ethoxy-acetic acid ethyl ester was hydrolyzed to give (RS)-N-(carboxy-ethoxy-methyl)-phthalamic acid. Off-white solid. MS 266.0 ($[M-H]^-$)

13.3

According to general procedure C, but using 2.2 eq. of BOP coupling reagent (RS)-N-(carboxy-ethoxy-methyl)-phthalamic acid was reacted with [(4-aminomethyl-phenyl)-imino-methyl]-carbamic acid benzyl ester to give (RS)-[1-amino-1-(4-{[2-(1,3-dioxo-1,3-dihydro-isoindol-2-yl)-2-ethoxy-acetylamino]-methyl}-phenyl)-meth-(Z)-ylidene]-carbamic acid benzyl ester dihydrochloride (CAS 172348-75-3). White solid. MS 515.3 ($[M+H]^+$)

13.4

According to general procedure E, (RS)-[1-amino-1-(4-{[2-(1,3-dioxo-1,3-dihydro-isoindol-2-yl)-2-ethoxy-acetylamino]-methyl}-phenyl)-meth-(Z)-ylidene]-carbamic acid benzyl ester was converted to (RS)-N-(4-carbamimidoyl-benzyl)-2-(1,3-dioxo-1,3-dihydro-isoindol-2-yl)-2-ethoxy-acetamide acetate. Off-white solid. MS 381.3 ($[M+H]^+$)

Example 14

14.1

Benzyl-1H-pyrazole-3-carbaldehyde (1.55 g, CAS 321405-31-6) and bromoform (0.94 ml) were dissolved under an argon atmosphere in dioxane/MeOH 1:1 (40 ml) and cooled to 0° C. A solution of KOH (2.31 g) in MeOH (20 ml) were added over a period of 20 min. The reaction was warmed to r.t. and stirred overnight. The reaction mixture was concentrated to one third of the volume, then taken up in water and washed with EtOAc. The aqueous layer was brought ot pH 1 with HCl, then extracted with EtOAc. The organic layer was washed with brine and concentrated to give crude (RS)-(1-benzyl-1H-pyrazol-3-yl)-methoxy-acetic acid (1.41 g). Yellow oil. MS 245.1 ([M−H]−)

14.2

Using analogous procedures as described in examples 1.3 and 1.4, (RS)-(1-benzyl-1H-pyrazol-3-yl)-methoxy-acetic acid was converted to (RS)-2-(1-benzyl-1H-pyrazol-3-yl)-N-(4-carbamimidoyl-benzyl)-2-methoxy-acetamide hydrochloride. White solid. MS 378.2 ([M+H]+)

Example 15

Using analogous procedures as described in example 14, 2-phenyl-oxazole-4-carbaldehyde (CAS 20771-08-8) was converted to (RS)-N-(4-carbamimidoyl-benzyl)-2-ethoxy-2-(2-phenyl-oxazol-4-yl)-acetamide acetate. Off-white solid. MS 379.2 ([M+H]+)

Example 16

16.1

A suspension of 5-methyl-1-phenyl-1H-[1,2,4]triazole-3-carboxylic acid (6.81 g, CAS 1016-57-5) in thionylchloride (48.6 ml) was heated to 80° C. (reflux) and stirring at that temperature was continued for 2 h 30. The mixture turned to a compact mass while heating. The mixture was concentrated and the residue (dark brown solid) was taken in EtOH (75 ml) and refluxed for 2 h 30. The mixture slowly turned to a dark red solution. After cooling to r.t., the mixture was concentrated. The crude product was isolated by chromatography (silica gel, 5% TEA in EtOAc) to give (RS)-5-methyl-1-phenyl-1H-[1,2,4]triazole-3-carboxylic acid ethyl ester (7.14 g) as brown oil. MS 232.2 ([M+H]+)

16.2

To a stirred, cooled (0° C.) solution of (RS)-5-methyl-1-phenyl-1H-[1,2,4]triazole-3-carboxylic acid ethyl ester (7.14 g) at r.t. in THF (200 ml) under an argon atmosphere was added dropwise a 1 M solution of LiAlH4 in THF (30.9 ml) for 10 min. When addition was complete, stirring at 0° C. was continued for 2 h 30. Water (2.4 ml), 15% NaOH (2.4 ml) and water (9.6 ml) were added dropwise to the cooled (0° C.) mixture. After 15 min stirring, the aluminium salts were filtered off and washed with EtOAc. The filtrate was diluted with EtOAc, washed with water and brine, dried (MgSO4), treated with decolorizing charcoal, filtered over a celite pad and concentrated. The crude product was isolated by chromatography (silica gel, gradient cyclohexane=>EtOAc) to give (5-methyl-1-phenyl-1H-[1,2,4]triazol-3-yl)-methanol (1.35 g, MS 190.4 ([M+H]+)) as an off-white solid and (RS)-(5-methyl-1-phenyl-4,5-dihydro-1H-[1,2,4]triazol-3-yl)-methanol (2.29 g, MS 191.1 ([M]+)) as a yellow solid.

16.3

To a stirred suspension of (RS)-(5-methyl-1-phenyl-4,5-dihydro-1H-[1,2,4]triazol-3-yl)-methanol (2.28 g) at r.t. in dichloromethane (75 ml) was added MnO2 (8.06 g). The black suspension was heated to reflux and stirring was continued for 24 h. The solids were filtered off and washed with CH2Cl2. The filtrate was concentrated. The crude product was purified by chromatography (silica gel, cyclohexane=>cyclohexane/EtOAc 1:4) to give 5-methyl-1-phenyl-1H-[1,2,4]triazole-3-carbaldehyde (0.78 g) as light yellow solid. MS 188.3 ([M+H]+)

Following the same procedure (5-methyl-1-phenyl-1H-[1,2,4]triazol-3-yl)-methanol was converted to 5-methyl-1-phenyl-1H-[1,2,4]triazole-3-carbaldehyde as well.

16.4

To a stirred solution of 5-methyl-1-phenyl-1H-[1,2,4]triazole-3-carbaldehyde (1.66 g) at r.t. in CH2Cl2 (50 ml) under an argon atmosphere were added zinc(II) iodide (65 mg) and trimethylsilyl cyanide (1.23 g). The yellow clear solution was then stirred at r.t. for 20 hrs and washed with water. The aqueous phase was extracted with CH2Cl2. The combined organics were washed with water and brine, dried (MgSO4), filtered and concentrated to give (RS)-(5-methyl-1-phenyl-1H-[1,2,4]triazol-3-yl)-trimethylsilanyloxy-acetonitrile (2.48 g) as brown oil. MS 287 ([M+H]+)

To a stirred solution of the crude (RS)-(5-methyl-1-phenyl-1H-[1,2,4]triazol-3-yl)-trimethylsilanyloxy-acetonitrile (2.47 g) in EtOH (20 ml) was added concentrated sulfuric acid (1.73 ml). The mixture was heated to reflux and stirring was continued for 17 h. After cooling to r.t., the mixture (light red clear solution) was poured into 50 ml of water. The solution was brought to pH~8 by the addition of saturated Na2CO3. It was extracted with EtOAc. The combined organic layers were washed with brine, dried (MgSO4), filtered and concentrated. The product was isolated by chromatography (silica gel, gradient cyclohexane=>EtOAc) to give (RS)-hydroxy-(5-methyl-1-phenyl-1H-[1,2,4]triazol-3-yl)-acetic acid ethyl ester (1.17 g) as off-white solid. MS 262.2 ([M+H]+)

16.5

To a stirred solution of (RS)-hydroxy-(5-methyl-1-phenyl-1H-[1,2,4]triazol-3-yl)-acetic acid ethyl ester (1.12 g) at r.t. in toluene (30 ml) under an argon atmosphere were added silver (I) oxide (2.99 g) and ethyl iodide (1.74 ml). The mixture was heated to reflux and stirring was continued for 16 h. The solids were filtered off and washed with EtOAc. The filtrate was concentrated. The product was isolated by chromatography (silica gel, gradient cyclohexane=>EtOAc) to give (RS)-ethoxy-(5-methyl-1-phenyl-1H-[1,2,4]triazol-3-yl)-acetic acid ethyl ester (0.87 g) as orange oil. MS 290.1 ([M+H]+)

16.6

According to general procedure B, (RS)-ethoxy-(5-methyl-1-phenyl-1H-[1,2,4]triazol-3-yl)-acetic acid ethyl ester was converted to (RS)-ethoxy-(5-methyl-1-phenyl-1H-[1,2,4]triazol-3-yl)-acetic acid. Light yellow solid. MS 260.0 ([M−H]−)

16.7

Using similar procedures as described in examples 9.1 to 9.3, (RS)-ethoxy-(5-methyl-1-phenyl-1H-[1,2,4]triazol-3-yl)-acetic acid was converted via (RS)-2-ethoxy-N-[4-(N-hydroxycarbamimidoyl)-benzyl]-2-(5-methyl-1-phenyl-1H-[1,2,4]triazol-3-yl)-acetamide (MS 409.5 ([M+H]+)) to (RS)-N-(4-carbamimidoyl-benzyl)-2-ethoxy-2-(5-methyl-1-phenyl-1H-[1,2,4]triazol-3-yl)-acetamide acetate. Off-white solid. MS 393.3 ([M+H]⁺)

Example 17

Using similar procedures as described in example 14, 1-methyl-2-formyl-benzimidazole (CAS 3012-80-4) was converted to (RS)-N-(4-carbamimidoyl-benzyl)-2-methoxy-2-(1-methyl-1H-benzoimidazol-2-yl)-acetamide acetate. Off-white solid. MS 352.3 ([M+H]⁺)

Example 18

18.1
Using an analogous procedure as described in example 14.1, 1-(2-trimethylsilanyl-ethoxymethyl)-1H-benzoimidazole-2-carbaldehyde (CAS 154028-50-9) was converted to (RS)-methoxy-[1-(2-trimethylsilanyl-ethoxymethyl)-1H-benzoimidazol-2-yl]-acetic acid. Orange solid. MS 337.3 ([M+H]⁺)

18.2
According to general procedure C, (RS)-methoxy-[1-(2-trimethylsilanyl-ethoxymethyl)-1H-benzoimidazol-2-yl]-acetic acid was reacted with [(4-aminomethyl-phenyl)-imino-methyl]-carbamic acid benzyl ester dihydrochloride (CAS 172348-75-3) to give (RS)-[1-amino-1-[4-({2-methoxy-2-[1-(2-trimethylsilanyl-ethoxymethyl)-1H-benzoimidazol-2-yl]-acetylamino}-methyl)-phenyl]-meth-(E)-ylidene]-carbamic acid benzyl ester. Light yellow solid. MS 602.3 ([M+H]⁺)

18.3
(RS)-[1-Amino-1-[4-({2-methoxy-2-[1 -(2-trimethylsilanyl-ethoxymethyl)-1H-benzoimidazol-2-yl]-acetylamino}-methyl)-phenyl]-meth-(E)-ylidene]-carbamic acid benzyl ester (0.5 g) was heated in 5 N HCl (20 ml) to 50° C. and stirring at that temperature was continued for 4 h. After cooling to r.t., the mixture was washed with EtOAc and cooled to 0° C. The pH was brought to ~12 by the dropwise addition of 4 N NaOH. The mixture was then extracted with EtOAc. The combined organics were washed with brine, dried (MgSO4), filtered and concentrated to give (RS)-[1-amino-1-(4-{[2-(1H-benzoimidazol-2-yl)-2-methoxy-acetylamino]-methyl}-phenyl)-meth-(E)-ylidene]-carbamic acid benzyl ester (0.258 g) as light yellow solid. MS472.3 ([M+H]⁺)

18.4
According to general method E, (RS)-[1-amino-1-(4-{[2-(1H-benzoimidazol-2-yl)-2-methoxy-acetylamino]-methyl}-phenyl)-meth-(E)-ylidene]-carbamic acid benzyl ester was converted to (RS)-2-(1H-benzoimidazol-2-yl)-N-(4-carbamimidoyl-benzyl)-2-methoxy-acetamide acetate. Off-white solid. MS 338.1 ([M+H]⁺)

Example 19

19.1
Sodium hydride (60% dispersion in mineral oil, 1.228 g=0.74 g NaH) was suspended in DMF (45 ml) under an argon atmosphere. The stirred suspension was cooled to 0° C. and 2-hydroxy-3-nitropyridine (4 g) was added portion wise over a period of 45 min. The mixture containing a compact yellow precipitate was then stirred at r.t. for 30 min and was cooled again to 0C. A solution of 2-chloro-2-ethoxyacetic acid ethyl ester (4.99 g) in DMF (5 ml) was then added and stirring at r.t. was continued for 2 h 30. The mixture was diluted with EtOAc and washed with water. The aqueous phase was extracted with EtOAc. The combined organics were washed with water and brine, dried (MgSO₄), filtered and concentrated. The crude product was purified by chromatography (silica gel, gradient cyclohexane=>cyclohexane/EtOAc 3:2) to give (RS)-ethoxy-(3-nitro-2-oxo-2H-pyridin-1-yl)-acetic acid ethyl ester (4.32 g) as yellow solid. MS 270.1 ([M]⁺)

19.2
To a stirred suspension of (RS)-ethoxy-(3-nitro-2-oxo-2H-pyridin-1-yl)-acetic acid ethyl ester (3.91 g) at r.t. in ethanol (25 ml) under an argon atmosphere was added 10% Pd/C (215 mg). The reaction mixture was then stirred at r.t. under a hydrogen atmosphere for 16 h. The catalyst was filtered off on a celite pad and washed with ethanol. The filtrate was concentrated. The crude product was purified by chromatography (silica gel, cyclohexane=>cyclohexane/EtOAc 2:3) to give (RS)-(3-amino-2-oxo-2H-pyridin-1-yl)-ethoxy-acetic acid ethyl ester as yellow oil. MS 241.2 ([M+H]⁺)

19.3
To a stirred, cooled (0° C.) solution (RS)-(3-amino-2-oxo-2H-pyridin-1-yl)-ethoxy-acetic acid ethyl ester (428 mg) and 2,4,6-collidine (0.47 ml) in THF (3 ml) under an argon atmosphere was added dropwise a solution of alpha-toluenesulphonylchloride (340 mg) in THF (2 ml) over 10 min. When addition was complete, stirring at 0° C. was continued for 2 h. The mixture was diluted with EtOAc, washed with 1.0 N HCl and brine, dried (MgSO₄), filtered and concentrated to give (RS)-ethoxy-(2-oxo-3-phenylmethanesulfonylamino-2H-pyridin-1-yl)-acetic acid ethyl ester (592 mg) as light brown solid. MS 393.0 ([M–H]⁻)

19.4
According to general procedure B, (RS)-ethoxy-(2-oxo-3-phenylmethanesulfonylamino-2H-pyridin-1-yl)-acetic acid ethyl ester was converted to (RS)-ethoxy-(2-oxo-3-phenylmethanesulfonylamino-2H-pyridin-1-yl)-acetic acid. MS 365.1 ([M–H]⁻)

19.5
Using similar procedures as described in examples 1.3 and 1.4, (RS)-ethoxy-(2-oxo-3-phenylmethanesulfonylamino-2H-pyridin-1-yl)-acetic acid was converted to (RS)-N-(4-carbamimidoyl-benzyl)-2-ethoxy-2-(2-oxo-3-phenylmethanesulfonylamino-2H-pyridin-1-yl)-acetamide acetate. Off-white solid. MS 496.3 ([M–H]⁻)

Example 20

Using similar procedure as described in examples 19.3 to 19.5, (RS)-(3-amino-2-oxo-2H-pyridin-1-yl)-ethoxy-acetic acid ethyl ester (example 19.2) was converted to (RS)-2-(3-benzenesulfonylamino-2-oxo-2H-pyridin-1-yl)-N-(4-carbamimidoyl-benzyl)-2-ethoxy-acetamide acetate. Off-white solid. MS 484.4 ([M+H]⁺)

Example 21

21.1
To a 100 ml flask was added in sequence molecular sieves 4Å(200 mg), phenylboronic acid (418 mg), CH₂Cl₂ (10 ml), triethylamine (0.48 ml), a solution of (RS)-(3-amino-2-oxo-2H-pyridin-1-yl)-ethoxy-acetic acid ethyl ester (412 mg, example 19.2) in CH$_2$Cl$_2$ (10 ml), cupric acetate (31 mg) and TEMPO (295 mg). A CaCl$_2$ trap was placed over the flask. The reaction was then stirred under air for 3 days. The solids were filtered off and washed with CH$_2$Cl$_2$. The filtrate was concentrated. The crude product was purified by chromatography (silica gel, gradient cyclohexane/EtOAc) to give (RS)-ethoxy-(2-oxo-3-phenylamino-2H-pyridin-1-yl)-acetic acid ethyl ester (258 mg) as green oil. MS 317.2 ([M+H]$^+$)

21.2

Using analogous procedures as described in examples 19.4 and 19.5, (RS)-ethoxy-(2-oxo-3-phenylamino-2H-pyridin-1-yl)-acetic acid ethyl ester was converted to (RS)-N-(4-carbamimidoyl-benzyl)-2-ethoxy-2-(2-oxo-3-phenylamino-2H-pyridin-1-yl)-acetamide acetate. Light green solid. MS 420.1 ([M+H]$^+$)

Example 22

22.1

Using an analogous procedure as described in example 21.1, (RS)-(3-amino-2-oxo-2H-pyridin-1-yl)-ethoxy-acetic acid ethyl ester (example 19.2) was reacted with 3-methoxy phenylboronic acid to give (RS)-ethoxy-[3-(3-methoxy-phenylamino)-2-oxo-2H-pyridin-1-yl]-acetic acid ethyl ester. Light green gum. MS 347.4 ([M+H]$^+$)

22.2

According to general procedure B, (RS)-ethoxy-[3-(3-methoxy-phenylamino)-2-oxo-2H-pyridin-1-yl]-acetic acid ethyl ester was converted to (RS)-ethoxy-[3-(3-methoxy-phenylamino)-2-oxo-2H-pyridin-1-yl]-acetic acid. Off-white powder.

22.3

Using analogous procedures as described in examples 8.2 and 8.3, (RS)-ethoxy-[3-(3-methoxy-phenylamino)-2-oxo-2H-pyridin-1-yl]-acetic acid was converted via (RS)-{amino-[4-({2-ethoxy-2-[3-(3-methoxy-phenylamino)-2-oxo-2H-pyridin-1-yl]-acetylamino}-methyl)-phenyl]-methylene}-carbamic acid benzyl ester (MS 583.3 ([M+H]$^+$)) to (RS)-N-(4-carbamimidoyl-benzyl)-2-ethoxy-2-[3-(3-methoxy-phenylamino)-2-oxo-2H-pyridin-1-yl]-acetamide acetate. Light green solid. MS 450.2 ([M+H]$^+$)

Example 23

Using analogous procedures as described in example 22, (RS)-(3-amino-2-oxo-2H-pyridin-1-yl)-ethoxy-acetic acid ethyl ester (example 19.2) was reacted with 3-fluorophenylboronic acid and then converted via (RS)-{amino-[4-({2-ethoxy-2-[3-(3-fluoro-phenylamino)-2-oxo-2H-pyridin-1-yl]-acetylamino}-methyl)-phenyl]-methylene}-carbamic acid benzyl ester (MS 572.3 ([M+H]$^+$)) to (RS)-N-(4-carbamimidoyl-benzyl)-2-ethoxy-2-[3-(3-fluoro-phenylamino)-2-oxo-2H-pyridin-1-yl]-acetamide acetate. Off-white solid. MS 438.2 ([M+H]$^+$)

Example 24

Using analogous procedures as described in example 22, (RS)-(3-amino-2-oxo-2H-pyridin-1-yl)-ethoxy-acetic acid ethyl ester (example 19.2) was reacted with 3-pyridylboronic acid and then converted via (RS)-{amino-[4-({2-ethoxy-2-[2-oxo-3-(pyridin-3-ylamino)-2H-pyridin-1-yl]-acetylamino}-methyl)-phenyl]-methylene}-carbamic acid benzyl ester (MS 555.2 ([M+H]+)) to (RS)-N-(4-carbamimidoyl-benzyl)-2-ethoxy-2-[2-oxo-3-(pyridin-3-ylamino)-2H-pyridin-1-yl]-acetamide acetate. Light green solid. MS 421.2 ([M+H]$^+$)

Example 25

25.1

According to general procedure B, the ester (RS)-ethoxy-(2-oxo-3-phenylamino-2H-pyridin-1-yl)-acetic acid ethyl ester (example 21.1) was hydrolysed. The corresponding acid was reacted with 4-aminomethyl-3-chloro-benzonitrile (CAS 202521-97-9) according to general procedure to give (RS)-N-(2-chloro-4-cyano-benzyl)-2-ethoxy-2-(2-oxo-3-phenylamino-2H-pyridin-1-yl)-acetamide. Light green solid. MS 437.1 ([M+H]$^+$)

25.2

Using analogous procedures as described in examples 9.2 and 9.3, (RS)-N-(2-chloro-4-cyano-benzyl)-2-ethoxy-2-(2-oxo-3-phenylamino-2H-pyridin-1-yl)-acetamide was converted via (RS)-N-[2-chloro-4-(N-hydroxycarbamimidoyl)-benzyl]-2-ethoxy-2-(2-oxo-3-phenylamino-2H-pyridin-1-yl)-acetamide (MS 470.2 ([M+H]$^+$)) to (RS)-N-(4-carbamimidoyl-2-chloro-benzyl)-2-ethoxy-2-(2-oxo-3-phenylamino-2H-pyridin-1-yl)-acetamide acetate. Light green powder. MS 454.2 ([M+H]$^+$)

Example 26

Using similar procedures as described in example 25, (RS)-ethoxy-(2-oxo-3-phenylamino-2H-pyridin-1-yl)-acetic acid ethyl ester (example 21.1) was hydrolyzed according to general procedure B. The corresponding acid was reacted according to general procedure C with 4-aminomethyl-2-chloro-benzonitrile (CAS 202522-15-4) and then converted via (RS)-N-[3-chloro-4-(N-hydroxycarbamimidoyl)-benzyl]-2-ethoxy-2-(2-oxo-3-phenylamino-2H-pyridin-1-yl)-acetamide (MS 470.2 ([M+H]$^+$)) to (RS)-N-(4-carbamimidoyl-3-chloro-benzyl)-2-ethoxy-2-(2-oxo-3-phenylamino-2H-pyridin-1-yl)-acetamide acetate. Light green solid. MS 454.2 ([M+H]$^+$)

Example 27

Using similar procedures as described in example 25, (RS)-ethoxy-(2-oxo-3-phenylamino-2H-pyridin-1-yl)-acetic acid ethyl ester (example 21.1) was hydrolyzed according to general procedure B. The corresponding acid was reacted according to general procedure C with 4-aminomethyl-3-fluoro-benzonitrile (prepared by analogous methods as described in U.S. Pat. No. 5,914,319) and then converted via (RS)-2-ethoxy-N-[2-fluoro-4-(N-hydroxycarbamimidoyl)-benzyl]-2-(2-oxo-3-phenylamino-2H-pyridin-1-yl)-acetamide (MS 454.2 ([M+H]$^+$)) to (RS)-N-(4-carbamimidoyl-2-fluoro-benzyl)-2-ethoxy-2-(2-oxo-3-phenylamino-2H-pyridin-1-yl)-acetamid; acetate. Light green solid. MS 438.2 ([M+H]$^+$)

Example 28

Using similar procedures as described in example 25, (RS)-ethoxy-(2-oxo-3-phenylamino-2H-pyridin-1-yl)-acetic acid ethyl ester (example 21.1) was hydrolyzed according to general procedure B. The corresponding acid was reacted according to general procedure C with 4-aminomethyl-2-fluoro-benzonitrile (CAS 368426-73-7) and then converted via (RS)-2-ethoxy-N-[3-fluoro-4-(N-hydroxycarbamimidoyl)-benzyl]-2-(2-oxo-3-phenylamino-2H-pyridin-1-yl)-acetamide (MS 454.2 ([M+H]$^+$)) to (RS)-N-(4-carbamimidoyl-3-fluoro-benzyl)-2-ethoxy-2-(2-oxo-3-phenylamino-2H-pyridin-1-yl)-acetamide acetate. Off-white powder. MS 438.2 ([M+H]$^+$)

Example 29

Using similar procedures as described in example 25, (RS)-ethoxy-(2-oxo-3-phenylamino-2H-pyridin-1-yl)-acetic acid ethyl ester (example 21.1) was hydrolyzed according to general procedure B. The corresponding acid was reacted according to general procedure C with 4-aminomethyl-2,6-difluoro-benzonitrile (prepared by analogous methods as described in U.S. Pat. No. 5,914,319) and then converted via (RS)-N-[2,6-difluoro-4-(N-hydroxycarbamimidoyl)-benzyl]-2-ethoxy-2-(2-oxo-3-phenylamino-2H-pyridin-1-yl)-acetamide (MS 472.2 ([M+H]$^+$)) to (RS)-N-(4-carbamimidoyl-2,6-difluoro-benzyl)-2-ethoxy-2-(2-oxo-3-phenylamino-2H-pyridin-1-yl)-acetamide acetate. Light green powder. MS 456.2 ([M+H]$^+$)

Example 30

Using similar procedures as described in example 25, (RS)-ethoxy-(2-oxo-3-phenylamino-2H-pyridin-1-yl)-acetic acid ethyl ester (example 21.1) was hydrolyzed according to general procedure B. The corresponding acid was reacted according to general procedure C with 6-aminomethyl-benzo[d]isoxazol-3-ylamine (CAS 368426-78-2) to give (RS)-N-(3-amino-benzo[d]isoxazol-6-ylmethyl)-2-ethoxy-2-(2-oxo-3-phenylamino-2H-pyridin-1-yl)-acetamide. Light green powder. MS 434.2 ([M+H]$^+$)

Example 31

Using similar procedures as described in example 25, (RS)-ethoxy-(2-oxo-3-phenylamino-2H-pyridin-1-yl)-acetic acid ethyl ester (example 21.1) was hydrolyzed according to general procedure B. The corresponding acid was reacted according to general procedure C with 6-aminomethyl-1H-indazol-3-ylamine (CAS 368426-75-9) to give (RS)-N-(3-amino-1H-indazol-6-ylmethyl)-2-ethoxy-2-(2-oxo-3-phenylamino-2H-pyridin-1-yl)-acetamide. Off-white solid. MS 433.3 ([M+H]$^+$)

Example 32

32.1
To a solution of 4-formyl-3-hydroxy-benzonitrile (CAS 84102-89-6) (6.90 g) in dry ethanol (165 ml) was added sodium acetate (4.23 g) and hydroxylamine hydrochloride (3.58 g). The mixture was stirred at r.t. for 1 h. The solvent was evaporated and the product was purified by flash chromatography (cyclohexane/EtOAc 8:2=>1:1) to give 3-hydroxy-4-(hydroxyimino-methyl)-benzonitrile (4.70 g). Light yellow solid. MS 162.0 ([M]$^+$)

32.2
A solution of 3-hydroxy-4-(hydroxyimino-methyl)-benzonitrile (1.79 g) in acetic acid (16.6 ml) was stirred at 65° C. Zinc powder (6.59 g) was added portionwise during 30 min. After stirring for a further 1.5 h, the reaction mixture was filtered and the filtrate was concentrated to dryness. 1 N HCl (55.3 ml) was added and the solvent was evaporated. The same procedure was repeated with with water (2x), EtOH (2x) and toluene (2x). The resulting colorless solid was dissolved in diethyl ether, filtered and the filtrate was concentrated to give 4-aminomethyl- 3-hydroxy-benzonitrile hydrochloride (colorless solid, 2.5 g) which was used in the next step without further purification. MS 149.2 ([M+H]$^+$)

32.3
To a solution of 4-aminomethyl-3-hydroxy-benzonitrile hydrochloride (2.0 g) and triethylamine (2.19 g) in dichloromethane (20 ml) was added di-tert-butyldicarbonate (2.41 g). The mixture was stirred at r.t. for 3.5 h. The mixture was washed with water (3x), dried, filtered and concentrated. The crude product was dissolved in DMF (15.5 ml). Cesium carbonate (4.00 g) and iodoacetamide (2.27 g) were added and the mixture was stirred at r.t. for 3 days. Water was added and the mixture was extracted with EtOAc. The organic phase was washed with water, dried, filtered and concentrated. The crude product was dissolved in MeOH and then concentrated to obtain a thick suspension. The solid was filtered off and washed with a small amount of MeOH. This procedure was repeated with the mother liquor to give (2-carbamoylmethoxy-4-cyano-benzyl)-carbamic acid tert-butyl ester (a total of 1.88 g) as a colorless solid. MS 304.2 ([M–H]$^-$)

32.4
The BOC protecting group of (2-carbamoylmethoxy-4-cyano-benzyl)-carbamic acid tert-butyl ester was removed using HCl in dioxane to give 2-(2-aminomethyl-5-cyano-phenoxy)-acetamide hydrochloride as an off-white powder. MS 206.1 ([M+H]$^+$)

32.5
(RS)-Ethoxy-(2-oxo-3-phenylamino-2H-pyridin-1-yl)-acetic acid ethyl ester (example 21.1) was hydrolyzed according to general procedure B. The corresponding acid was reacted according to general procedure C with 2-(2-aminomethyl-5-cyano-phenoxy)-acetamide hydrochloride and then converted via (RS)-N-[2-carbamoyl methoxy-4-(N-hydroxycarbamimidoyl)-benzyl]-2-ethoxy-2-(2-oxo-3-phenylamino-2H-pyridin-1-yl)-acetamide (MS 509.6 5 ([M+H]$^+$)) to (RS)-N-(4-carbamimidoyl-2-carbamoyl-methoxy-benzyl)-2-ethoxy-2-(2-oxo-3-phenylamino-2H-pyridin-1-yl)-acetamide acetate. Light green powder. MS 493.5 ([M+H]$^+$)

Example 33

Using analogous procedures as described in examples 1.2 to 1.4, ethoxy-(6-methyl-2-oxo-1,2-dihydro-pyridin-3-yl)-acetic acid ethyl ester (CAS 78440-92-3) was converted to (RS)-N-(4-carbamimidoyl-benzyl)-2-ethoxy-2-(6-methyl-2-oxo-1,2-dihydro-pyridin-3-yl)-acetamide hydrochloride. MS 343.2 ([M+H]$^+$)

Example 34

Using analogous procedures as described in examples 1.2 to 1.4, ethoxy-(6-methyl-2-oxo-1,2-dihydro-pyridin-3-yl)-acetic acid ethyl ester (prepared from 2-oxo-6-phenyl-2,3-dihydro-pyridine-3-carbonitrile (CAS 43083-13-2) following a procedure described in J. Heterocycl. Chem. (1981), p.367) was converted to (RS)-N-(4-carbamimidoyl-benzyl)-2-ethoxy-2-(2-oxo-6-phenyl-1,2-dihydro-pyridin-3-yl)-acetamide hydrochloride. Off-white solid. MS 405.3 ([M+H]$^+$)

Example 35

35.1
According to general procedure H, 4-fluoro-1H-isoindole-1,3(2H)-dione (CAS51108-29-3) was reacted with 2-chloro-2-ethoxyacetic acid ethyl ester to give (RS)-ethoxy-(4-fluoro-1,3-dioxo-1,3-dihydro-isoindol-2-yl)-acetic acid ethyl ester, MS 296.3 ([M+H]$^+$).

35.2
According to general procedure B, (RS)-ethoxy-(4-fluoro-1,3-dioxo-1,3-dihydro-isoindol-2-yl)-acetic acid ethyl ester was hydrolyzed to give a mixture of (RS)-N-(ethoxy-ethoxycarbonyl-methyl)-6-fluoro-phthalamic acid and its regioisomer (RS)-N-(ethoxy-ethoxycarbonyl-methyl)-3-fluoro-phthalamic acid.

35.3
According to general procedure C, but using 2.2 eq. of BOP coupling reagent and adding the amine component after a delay time of 1 h, (RS)-N-(ethoxy-ethoxycarbonyl-methyl)-6-fluoro-phthalamic acid and its regioisomer (RS)-N-(ethoxy-ethoxycarbonyl-methyl)-3-fluoro-phthalamic acid was reacted with [1-amino-1-(4-aminomethyl-phenyl)-meth-(Z)-ylidene]-carbamic acid benzyl ester to give (RS)-[1-amino-1-(4-{[2-ethoxy-2-(4-fluoro-1,3-dioxo-1,3-dihydro-isoindol-2-yl)-acetylamino]-methyl}-phenyl)-meth-(Z)-ylidene]-carbamic acid benzyl ester, MS 533.4 ([M+H]$^+$).

35.4
According to general procedure E, (RS)-[1-amino-1-(4-{[2-ethoxy-2-(4-fluoro-1,3-dioxo-1,3-dihydro-isoindol-2-yl)-acetylamino]-methyl}-phenyl)-meth-(Z)-ylidene]-carbamic acid benzyl ester was converted to (RS)-N-(4-carbamimidoyl-benzyl)-2-ethoxy-2-(4-fluoro-1,3-dioxo-1,3-dihydro-isoindol-2-yl)-acetamide, isolated as acetate; white crystals, MS 399.3 ([M+H]$^+$).

Example 36

Using similar procedures as described in example 35, 5-methyl-isoindole-1,3-dione (CAS 40314-06-5) was transformed into (RS)-N-(4-carbamimidoyl-benzyl)-2-ethoxy-2-(5-methyl-1,3-dioxo-1,3-dihydro-isoindol-2-yl)-acetamide; white crystals, MS 395.3 ([M+H]$^+$).

Example 37

Using similar procedures as described in example 35, 4-methyl-isoindole-1,3-dione (CAS 7251-82-3) was converted into (RS)-N-(4-carbamimidoyl-benzyl)-2-ethoxy-2-(4-methyl-1,3-dioxo-1,3-dihydro-isoindol-2-yl)-acetamide; off-white crystals, MS 395.3 ([M+H]$^+$).

Example 38

Using similar procedures as described in example 35, 4,7-difluoro-isoindole-1,3-dione (CAS 196956-23-7) was transformed into (RS)-N-(4-carbamimidoyl-benzyl)-2-(4,7-difluoro-1,3-dioxo-1,3-dihydro-isoindol-2-yl)-2-ethoxy-acetamide, isolated as acetate; light brown solid, MS 417.3 ([M+H]$^+$).

Example 39

Using similar procedures as described in example 35, 5-tert-butyl-isoindole-1,3-dione (CAS 50727-07-6) was converted into (RS)-2-(5-tert-butyl-1,3-dioxo, 1,3-dihydro-isoindol-2-yl)-N-(4-carbamimidoyl-benzyl)-2-ethoxy-acetamide, light brown foam, MS 437.4 ([M+H]$^+$).

Example 40

40.1
According to general procedure H, 6-methyl-2,3-dihydro-isoindol-1-one (CAS 58083-55-9), together with its regioisomer 5-methyl-2,3-dihydro-isoindol-1-one (CAS 65399-03-3), was reacted with 2-chloro-2-ethoxyacetic acid ethyl ester to give, after chromatographic separation of the isomers, (RS)-ethoxy-(6-methyl-1-oxo-1,3-dihydro-isoindol-2-yl)-acetic acid ethyl ester, MS 232.0 ([M−EtO]$^+$).

40.2
According to general procedure B, (RS)-ethoxy-(6-methyl-1-oxo-1,3-dihydro-isoindol-2-yl)-acetic acid ethyl ester was hydrolyzed to give (RS)-ethoxy-(6-methyl-1-oxo-1,3-dihydro-isoindol-2-yl)-acetic acid, MS 248.0 ([M−H]$^-$).

40.3
According to general procedure C, (RS)-ethoxy-(6-methyl-1-oxo-1,3-dihydro-isoindol-2-yl)-acetic acid was reacted with [1-amino-1-(4-aminomethyl-phenyl)-meth-(Z)-ylidene]-carbamic acid benzyl ester to give (RS)-[1-amino-1-(4-{[2-ethoxy-2-(6-methyl-1-oxo-1,3-dihydro-isoindol-2-yl)-acetylamino]-methyl}-phenyl)-meth-(Z)-ylidene]-carbamic acid benzyl ester as light yellow foam, MS 515.5 ([M+H]$^+$).

40.4
According to general procedure E, (RS)-[1-amino-1-(4-{[2-ethoxy-2-(6-methyl-1-oxo-1,3-dihydro-isoindol-2-yl)-acetylamino]-methyl}-phenyl)-meth-(Z)-ylidene]-carbamic acid benzyl ester was converted to (RS)-N-(4-carbamimidoyl-benzyl)-2-ethoxy-2-(6-methyl-1-oxo-1,3-dihydro-isoindol-2-yl)-acetamide, isolated as acetate; off-white solid, MS 381.3 ([M+H]$^+$).

Example 41

Using similar procedures as described in example 40, 5-methyl-2,3-dihydro-isoindol-1-one (CAS 65399-03-3) was converted into (RS)-N-(4-carbamimidoyl-benzyl)-2-ethoxy-2-(5-methyl-1-oxo-1,3-dihydro-isoindol-2-yl)-acetamide, isolated as acetate; off-white solid, MS 381.3 ([M+H]$^+$).

Example 42

Using similar procedures as described in example 40, 4-fluoro-2,3-dihydro-isoindol-1-one (CAS 366452-96-2) was transformed into (RS)-N-(4-carbamimidoyl-benzyl)-2-ethoxy-2-(4-fluoro-1-oxo-1,3-dihydro-isoindol-2-yl)-acetamide, isolated as acetate; white crystals, MS 385.2 ([M+H]$^+$).

Example 43

Using similar procedures as described in example 40, 4,7-difluoro-2,3-dihydro-isoindol-1-one was converted into (RS)-N-(4-carbamimidoyl-benzyl)-2-(4,7-difluoro-1-oxo-1,3-dihydro-isoindol-2-yl)-2-ethoxy-acetamide, isolated as acetate; light brown solid, MS 403.4 ([M+H]$^+$).

The starting material was prepared as follows:

To a solution of 4,7-difluoro-isoindole-1,3-dione (CAS 196956-23-7, 0.253 g) in 6.9 ml of ethanol was added NaBH$_4$ (0.052 g) and the mixture stirred at ambient temperature. Pouring onto crashed ice, twofold extraction with AcOEt, washing with water, and drying over sodium sulfate left 0.219 g of a yellow wax (MS 183.9 ([M–H]$^-$)), which was further reduced as stated below.

0.216 g thereof was dissolved in trifluoroacetic acid (5.6 ml) and treated with 10 eq. of Et$_3$SiH. The mixture was kept for 3 h at ambient temperature, when TLC indicated the disappearance of starting material. Pouring onto crushed ice/NaHCO$_3$-solution, twofold extraction with AcOEt, washing with water, drying over sodium sulfate, and evaporation of the solvents, followed by flash chromatography (SiO$_2$, AcOEt), yielded 0.128 g of 4,7-difluoro-2,3-dihydro-isoindol-1-one as white solid, MS 196.0 ([M]$^+$).

Example 44

Using similar procedures as described in example 40, 4-methyl-2,3-dihydro-isoindol-1-one (CAS 65399-01-1) was converted via (RS)-ethoxy-(4-methyl-1-oxo-1,3-dihydro-isoindol-2-yl)-acetic acid into (RS)-N-(4-carbamimidoyl-benzyl)-2-ethoxy-2-(4-methyl-1-oxo-1,3-dihydro-isoindol-2-yl)-acetamide, isolated as acetate; white crystals, MS 381.3 ([M+H]$^+$).

Example 45

Using similar procedures as described in example 40, 7-methyl-2,3-dihydro-isoindol-1-one (CAS 65399-02-2) was processed into (RS)-N-(4-carbamimidoyl-benzyl)-2-ethoxy-2-(7-methyl-1-oxo-1,3-dihydro-isoindol-2-yl)-acetamide, isolated as acetate; white crystals, MS 381.3 ([M+H]$^+$).

Example 46

46.1
According to general procedure C, (RS)-ethoxy-(4-methyl-1-oxo-1,3-dihydro-isoindol-2-yl)-acetic acid (intermediate of example 44) was coupled with 4-aminomethyl-3-nitrobenzonitrile (CAS 701269-65-0) to give (RS)-N-(4-cyano-2-nitro-benzyl)-2-ethoxy-2-(4-methyl-1-oxo-1,3-dihydro-isoindol-2-yl)-acetamide as off-white crystals, MS 409.4 ([M+H]$^+$).

46.2
To a solution of (RS)-N-(4-cyano-2-nitro-benzyl)-2-ethoxy-2-(4-methyl-1-oxo-1,3-dihydro-isoindol-2-yl)-acetamide (0.382 g) in ethyl acetate (9 ml) was added 10% Pd/C (190 mg) and the mixture vigorously stirred at r.t. under a hydrogen atmosphere for 16 h. The catalyst was filtered over a celite pad and the cake was carefully washed with ethyl acetate. The filtrate was evaporated to yield (RS)-N-(2-amino-4-cyano-benzyl)-2-ethoxy-2-(4-methyl-1-oxo-1,3-dihydro-isoindol-2-yl)-acetamide (0.354 g) as off-white foam, MS 379.4 ([M+H]$^+$).

46.3
(RS)-N-(2-Amino-4-cyano-benzyl)-2-ethoxy-2-(4-methyl-1-oxo-1,3-dihydro-isoindol-2-yl)-acetamide (0.101 g) was treated in MeOH (2 ml) successively with 2-fluoro-benzaldehyde (99 mg) and 1 ml of a MeOH-solution containing scrupulously dried ZnCl$_2$ (145 mg) and NaCNBH$_3$ (50 mg). The reaction mixture was stirred for 16 h at 50–55° C., poured onto crashed ice and extracted two times with ethyl acetate. The combined organic layers were washed with water and brine and dried over magnesium sulfate. The solvent was removed under reduced pressure and the residue purified by column chromatography (silica gel, hexane/AcOEt=1/1) to give (RS)-N-[4-cyano-2-(2-fluoro-benzylamino)-benzyl]-2-ethoxy-2-(4-methyl-1-oxo-1,3-dihydro-isoindol-2-yl)-acetamide (111 mg) as colorless oil, MS 487.4 ([M+H]$^+$).

46.4
According to general procedure F and slightly modified procedure G (10% Pd/C instead of Raney Ni as catalyst) (RS)-N-[4-cyano-2-(2-fluoro-benzylamino)-benzyl]-2-ethoxy-2-(4-methyl-1-oxo-1,3-dihydro-isoindol-2-yl)-acetamide was converted into (RS)-N-[4-carbamimidoyl-2-(2-fluoro-benzylamino)-benzyl]-2-ethoxy-2-(4-methyl-1-oxo-1,3-dihydro-isoindol-2-yl)-acetamide, isolated as acetate; off-white crystals, MS 562.4 ([M+OAc]$^+$).

Example 47

Using similar procedures as described in example 46, (RS)-ethoxy-(7-methyl-1-oxo-1,3-dihydro-isoindol-2-yl)-acetic acid (intermediate of example 45) was processed into (RS)-N-[4-carbamimidoyl-2-(2-fluoro-benzylamino)-benzyl]-2-ethoxy-2-(7-methyl-1-oxo-1,3-dihydro-isoindol-2-yl)-acetamide, isolated as acetate; white solid, MS 504.5 ([M+H]$^+$).

Example 48

Using similar procedures as described in example 46, (RS)-ethoxy-(4-fluoro-1-oxo-1,3-dihydro-isoindol-2-yl)-acetic acid (intermediate of example 42) was transformed into (RS)-N-[4-carbamimidoyl-2-(2-fluoro-benzylamino)-benzyl]-2-ethoxy-2-(4-fluoro-1-oxo-1,3-dihydro-isoindol-2-yl)-acetamide, isolated as acetate; off-white solid, MS 508.6 ([M+H]$^+$).

Example 49

Using similar procedures as described in example 48, but using for the reductive amination acetaldehyde instead of 2-fluorobenzaldehyde, (RS)-ethoxy-(4-fluoro-1-oxo-1,3-dihydro-isoindol-2-yl)-acetic acid (intermediate of example 42) was converted into (RS)-N-(4-carbamimidoyl-2-ethylamino-benzyl)-2-ethoxy-2-(4-fluoro-1-oxo-1,3-dihydro-isoindol-2-yl)-acetamide, isolated as acetate; light brown solid, MS 428.4 ([M+H]$^+$).

Example 50

50.1
Using similar procedures as described in example 48, but using for the reductive amination methyl 4-formylbenzoate instead of 2-fluorobenzaldehyde, (RS)-ethoxy-(4-fluoro-1-oxo-1,3-dihydro-isoindol-2-yl)-acetic acid (intermediate of example 42) was transformed into (RS)-4-[(5-cyano-2-{[2-ethoxy-2-(4-fluoro-1-oxo-1,3-dihydro-isoindol-2-yl)-acetylamino]-methyl}-phenylamino)-methyl]-benzoic acid methyl ester, light yellow oil, MS 531.3 ([M+H]$^+$).

50.2
According to general procedure D, but using CHCl$_3$/MeOH 1:1 as solvent mixture, (RS)-4-[(5-cyano-2-{[2-ethoxy-2-(4-fluoro-1-oxo-1,3-dihydro-isoindol-2-yl)-acetylamino]-methyl}-phenylamino)-methyl]-benzoic acid methyl ester was converted into (RS)-4-[(5-carbamimidoyl-2-{[2-(4-fluoro-1-oxo-1,3-dihydro-isoindol-2-yl)-2-methoxy-acetylamino]-methyl}-phenylamino)-methyl]-benzoic acid methyl ester, isolated as acetate; light brown solid, MS 534.5 ([M+H]$^+$). Please note that under the Pinner conditions, the ethoxy group was replaced by methoxy!

Example 51

Using similar procedures as described in example 49 and 50, (RS)-ethoxy-(4-methyl-1-oxo-1,3-dihydro-isoindol-2-yl)-acetic acid (intermediate of example 44) was converted into (RS)-N-(4-carbamimidoyl-2-ethylamino-benzyl)-2-ethoxy-2-(4 -methyl-1-oxo-1,3-dihydro-isoindol-2-yl)-acetamide, isolated as acetate; light brown foam, MS 424.4 ([M+H]$^+$). For the last step, the transformation of the nitrile into the amidine, again Pinner conditions were chosen, this time, however, in ethanol instead of methanol!

Example 52

Using similar procedures as described in example 48, 6-chloro-2,3-dihydro-isoindol-1-one (CAS 58083-59-3) was transformed via (RS)-(6-chloro-1-oxo-1,3-dihydro-isoindol-2-yl)-ethoxy-acetic acid into (RS)-N-[4-carbamimidoyl-2-(2-fluoro-benzylamino)-benzyl]-2-(6-chloro-1-oxo-1,3-dihydro-isoindol-2-yl)-2-ethoxy-acetamide, isolated as acetate; white crystals, MS 524.4 ([M+H]$^+$).

Example 53

Using similar procedures as described in example 49, (RS)-(6-chloro-1-oxo-1,3-dihydro-isoindol-2-yl)-ethoxy-acetic acid (intermediate of example 52) was converted into (RS)-N-(4-carbamimidoyl-2-ethylamino-benzyl)-2-(6-chloro-1-oxo-1,3-dihydro-isoindol-2-yl)-2-ethoxy-acetamide, isolated as acetate; light brown waxy solid, MS 444.4 ([M+H]$^+$).

Example 54

Using similar procedures as described in example 49, 5-methoxy-2,3-dihydro-isoindol-1-one (CAS 22246-66-8) was converted via (RS)-ethoxy-(5-methoxy-1-oxo-1,3-dihydro-isoindol-2-yl)-acetic acid into (RS)-N-(4-carbamimidoyl-2-ethylamino-benzyl)-2-ethoxy-2-(5-methoxy-1-oxo-1,3-dihydro-isoindol-2-yl)-acetamide, isolated as hydrochloride; white powder, MS 440.5 ([M+H]$^+$).

Example 55

Using similar procedures as described in example 55, but omitting the reductive amination step, 5-methoxy-2,3-dihydro-isoindol-1-one (CAS 22246-66-8) was converted into (RS)-N-(2-amino-4-carbamimidoyl-benzyl)-2-ethoxy-2-(5-methoxy-1-oxo-1,3-dihydro-isoindol-2-yl)-acetamide, isolated as diacetate; off-white solid, MS 412.4 ([M+H]$^+$).

Example 56

Using similar procedures as described in example 54, 6-piperidin-1-yl-2,3-dihydro-isoindol-1-one was transformed via (RS)-ethoxy-(1-oxo-6-piperidin-1-yl-1,3-dihydro-isoindol-2-yl)-acetic acid into (RS)-N-(4-carbamimidoyl-2-ethylamino-benzyl)-2-ethoxy-2-(1-oxo-6-piperidin-1-yl-1,3-dihydro-isoindol-2-yl)-acetamide, isolated as acetate; off-white foam, MS 493.6 ([M+H]$^+$).

The starting material was prepared as follows:

6-Amino-2,3-dihydro-isoindol-1-one (0.810 g, CAS 675109-45-2) was dissolved in 12 ml of acetonitrile and treated successively with sodium iodide (2.458 g, 3 eq.), 1,5-dibromopentane (1.11 ml, 1.5 eq.), and N-ethyl-diisopropylamine (2.88 ml, 3.1 eq.), and the mixture was stirred at 75° C. for 20 h. Pouring onto crushed ice, twofold extraction with AcOEt, washing with water and brine, drying over magnesium sulfate, and evaporation of the solvents, followed by crystallization from hexane/ethyl acetate yielded 6-piperidin-1-yl-2,3-dihydro-isoindol-1-one (0.669 g) as light brown crystals, MS 217.3 ([M+H]$^+$).

Example 57

Relying on similar procedures as described in example 56, but using for the reductive amination 2-fluorobenzaldehyde instead of acetaldehyde, 6-piperidin-1-yl-2,3-dihydro-isoindol-1-one was transformed via (RS) -ethoxy-(1-oxo-6-piperidin-1-yl-1,3-dihydro-isoindol-2-yl)-acetic acid into (RS)-N-[4-carbamimidoyl-2-(2 -fluoro-benzylamino)-benzyl]-2-ethoxy-2-(1-oxo-6-piperidin-1-yl-1,3-dihydro-isoindol-2-yl)-acetamide, isolated as acetate; off-white solid, MS 573.5 ([M+H]$^+$).

Example 58

Using similar procedures as described in example 56, 6-pyrrolidin-1-yl-2,3-dihydro-isoindol-1-one was converted via (RS)-ethoxy-(1-oxo-6-pyrrolidin-1-yl-1,3-dihydro-isoindol-2-yl)-acetic acid into (RS)-N-(4-carbamimidoyl-2-ethylamino-benzyl)-2-ethoxy-2-(1-oxo-6-pyrrolidin-1-yl-1,3-dihydro-isoindol-2-yl)-acetamide, isolated as hydrochloride; light yellow crystals, MS 479.5 ([M+H]$^+$).

The starting material 6-pyrrolidin-1-yl-2,3-dihydro-isoindol-1-one was prepared from 6-amino-2,3-dihydro-isoindol-1-one (CAS 675109-45-2) and 1,4-dibromobutane in analogy to the precedure described in example 56.

Example 59

Relying on similar procedures as described in example 58, but using for the reductive amination 2-fluorobenzaldehyde instead of acetaldehyde, 6-pyrrolidin-1-yl-2,3-dihy-dro-isoindol-1-one was converted via (RS)-ethoxy-(1-oxo-6-pyrrolidin-1-yl-1,3-dihydro-isoindol-2-yl)-acetic acid into (RS)-N-[4-carbamimidoyl-2-(2-fluoro-benzylamino)-benzyl]-2-ethoxy-2-(1-oxo-6-pyrrolidin-1-yl-1,3-dihydro-isoindol-2-yl)-acetamide, isolated as acetate; off-white solid, MS 559.6 ([M+H]+).

Example 60

60.1

According to general procedure C, but using 2.2 eq. of BOP coupling reagent and adding the amine component after a delay time of 1 h, (RS)-N-(ethoxy-ethoxycarbonyl-methyl)-6-fluoro-phthalamic acid and its regioisomer (RS)-N-(ethoxy-ethoxycarbonyl-methyl)-3-fluoro-phthalamic acid (example 35.2) was reacted with 4-aminomethyl-3-nitrobenzonitrile (CAS 701269-65-0) to give (RS)-N-(4-cyano-2-nitro-benzyl)-2-ethoxy-2-(4-fluoro-1,3-dioxo-1,3-dihydro-isoindol-2-yl)-acetamide as yellow viscous oil which was further processed as follows, MS 427.3 ([M+H]$^+$).

60.2

To a solution of (RS)-N-(4-cyano-2-nitro-benzyl)-2-ethoxy-2-(4-fluoro-1,3-dioxo-1,3-dihydro-isoindol-2-yl)-acetamide (0.310 g) in ethyl acetate (7.3 ml) was added 10% Pd/C (60 mg) and the mixture vigorously stirred at r.t. under a hydrogen atmosphere for 24 h. The catalyst was filtered off over a celite pad and the cake was carefully washed with ethyl acetate. The filtrate was evaporated to yield (RS)-N-(2-amino-4-cyano-benzyl)-2-ethoxy-2-(4-fluoro-1,3-dioxo-1,3-dihydro-isoindol-2-yl)-acetamide (0.293 g) as yellow viscous oil, MS 397.2 ([M+H]$^+$).

60.3

(RS)-N-(2-amino-4-cyano-benzyl)-2-ethoxy-2-(4-fluoro-1,3-dioxo-1,3-dihydro-isoindol-2-yl)-acetamide (0.060 g) was treated in MeOH (1 ml) successively with 2-fluorobenzaldehyde (56 mg) and 1 ml of a MeOH-solution containing scrupulously dried ZnCl$_2$ (83 mg) and NaCNBH$_3$ (29 mg). The reaction mixture was stirred for 6 h at 50–55° C., poured onto crashed ice and extracted two times with ethyl acetate. The combined organic layers were washed with water and brine and dried over magnesium sulfate. The solvent was removed under reduced pressure and the residue purified by column chromatography (silica gel, hexane/AcOEt=6/4) to yield (RS)-N-[4-cyano-2-(2-fluoro-benzylamino)-benzyl ]-2-ethoxy-2-(4-fluoro-1,3-dioxo-1,3-dihydro-isoindol-2-yl)-acetamide (58 mg) as yellow oil, MS 505.4 ([M+H]$^+$).

60.4

A modified Pinner-procedure was used as followes:

Dry HCl gas was passed over a cooled (−10° C.), stirred solution of (RS)-N-[4-cyano-2-(2-fluoro-benzylamino)-benzyl]-2-ethoxy-2-(4-fluoro-1,3-dioxo-1,3 -dihydro-isoindol-2-yl)-acetamide (57 mg) in CHCl$_3$/EtOH 5:1 for 10 min. The flask was stoppered and left at 4° C. overnight. The reaction mixture was then distributed between AcOEt and a cold aqueous layer whose pH was adjusted with NaHCO$_3$ to 7. The organic phase was dried over sodium sulfate and evaporated to dryness. The resultant intermediate was dissolved in MeOH (3.5 ml) and treated with NH$_4$Cl solution (75 mg) in water (0.75 ml). This mixture was stirred at 65° C. for 3.5 h, diluted with acetone to precipitate the NH$_4$Cl, and filtrated. The thereby obtained crude product was purified by chromatography (silica gel, AcOEt/acetone/AcOH/water=6/2/1/1) to afford (RS)-N-[4-carbamimidoyl-2-(2-fluoro-benzylamino)-benzyl]-2-ethoxy-2-(4-fluoro-1,3-dioxo-1,3-dihydro-isoindol-2-yl)-acetamide (23 mg), isolated as acetate; light yellow solid, MS 522.4 ([M+H]$^+$).

Example 61

Using similar procedures as described in example 60, 5-methyl-isoindole-1,3-dione (CAS 40314-06-5) was converted into (RS)-N-[4-carbamimidoyl-2-(2-fluoro-benzylamino)-benzyl]-2-ethoxy-2-(5-methyl-1,3-dioxo-1,3-dihydro-isoindol-2-yl)-acetamide, isolated as acetate; light yellow crystals, MS 518.3 ([M+H]$^+$).

Example 62

Relying on similar procedures as described in example 61, but using for the reductive amination 4-formyl-benzoic acid methyl ester instead of 2-fluorobenzaldehyde, 5-methyl-isoindole-1,3-dione (CAS 40314-06-5) was converted into (RS)-4-[(5-carbamimidoyl-2-{[2-ethoxy-2-(5-methyl-1,3-dioxo-1,3-dihydro-isoindol-2-yl)-acetylamino]-methyl}-phenylamino)-methyl]-benzoic acid methyl ester, isolated as acetate; light yellow crystals, MS 558.4 ([M+H]$^+$).

Example 63

63.1

According to general procedure C, (RS)-ethoxy-(4-methyl-1-oxo-1,3-dihydro-isoindol-2-yl)-acetic acid (intermediate of example 44) was coupled with 4-formyl-3-hydroxy-benzonitrile (CAS 84102-89-6) to produce (RS)-N-(4-cyano-2-hydroxy-benzyl)-2-ethoxy-2-(4-methyl-1-oxo-1,3-dihydro-isoindol-2-yl)-acetamide, off-white solid, MS 380.4 ([M+H]$^+$).

63.2

(RS)-N-(4-Cyano-2-hydroxy-benzyl)-2-ethoxy-2-(4-methyl-1-oxo-1,3-dihydro-isoindol-2-yl)-acetamide (300 mg) was dissolved in acetonitrile (10 ml) and treated over night under vigorous stirring at ambient temperature with iodoacetamide (223 mg) and cesium carbonate (411 mg). Pouring onto crushed ice/NH$_4$Cl, twofold extraction with AcOEt, washing with brine, drying over sodium sulfate, and evaporation of the solvents, followed by flash column chromatography (silica gel, AcOEt/MeOH=10/1), afforded 75 mg of (RS)-N-(2-carbamoylmethoxy-4-cyano-benzyl)-2-ethoxy-2-(4-methyl-1-oxo-1,3-dihydro-isoindol-2-yl)-acetamide as white solid, MS 437.4 ([M+H]$^+$).

63.3

Following general procedure D, (RS)-N-(2-carbamoylmethoxy-4-cyano-benzyl)-2-ethoxy-2-(4-methyl-1-oxo-1,3-dihydro-isoindol-2-yl)-acetamide was transformed into (RS)-N-(4-carbamimidoyl-2-carbamoylmethoxy-benzyl)-2-ethoxy-2-(4-methyl-1-oxo-1,3-dihydro-isoindol-2-yl)-acetamide, isolated as acetate; off-white solid, MS 454.5 ([M+H]$^+$).

Example 64

64.1

Using similar procedures as described in example 63, 5-methoxy-2,3-dihydro-isoindol-1-one (CAS 22246-66-8) was converted via (RS)-N-(4-cyano-2-hydroxy-benzyl)-2-ethoxy-2-(5-methoxy-1-oxo-1,3-dihydro-isoindol-2-yl)-acetamide into (RS )-N-(2-carbamoylmethoxy-4-cyano-benzyl)-2-ethoxy-2-(5-methoxy-1-oxo-1,3-dihydro-isoindol-2-yl)-acetamide, white solid, MS 453.4 ([M+H]$^+$).

64.2

Following general procedures F and slightly modified procedure G (10% Pd/C instead of Raney Ni as catalyst), (RS)-N-(2-carbamoylmethoxy-4-cyano-benzyl)-2-ethoxy-2-(5-methoxy-1-oxo-1,3-dihydro-isoindol-2-yl)-acetamide was transformed into (RS)-N-(4-carbamimidoyl-2-carbamoylmethoxy-benzyl)-2-ethoxy-2-(5-methoxy-1-oxo-1,3-dihydro-isoindol-2-yl)-acetamide, isolated as acetate; light brown solid, MS 470.4 ([M+H]$^+$).

Example 65

65.1

(RS)-N-(4-Cyano-2-hydroxy-benzyl)-2-ethoxy-2-(5-methoxy-1-oxo-1,3-dihydro-isoindol-2-yl)-acetamide (intermediate of example 64, 101 mg) was dissolved in acetonitrile (2.2 ml) and treated over night under vigorous stirring at 40° C. with 2-chloro-N-methylacetamide (29 mg), potassium iodide (42 mg), and cesium carbonate (92 mg). Pouring onto crashed ice/NH$_4$Cl, twofold extraction with AcOEt, washing with water, drying over sodium sulfate, and evaporation of the solvents, followed by flash column chromatography (silica gel, AcOEt), yielded (RS )-N-(4-cyano-2-methylcarbamoyl methoxy-benzyl)-2-ethoxy-2-(5-methoxy-1-oxo-1,3-dihydro-isoindol-2-yl)-acetamide (113 mg), off-white solid, MS 467.4 ([M+H]$^+$).

65.2

Following general procedure D, (RS)-N-(4-cyano-2-methylcarbamoylmethoxy-benzyl)-2-ethoxy-2-(5-methoxy-1-oxo-1,3-dihydro-isoindol-2-yl)-acetamide was converted into (RS)-N-(4-carbamimidoyl-2-methylcarbamoyl-methoxy-benzyl)-2-ethoxy-2-(5-methoxy-1-oxo-1,3-dihydro-isoindol-2-yl)-acetamide, isolated as acetate; off-white solid, MS 484.5 ([M+H]$^+$).

Example 66

66.1

A 0.1 M solution under N$_2$ of iPr$_2$NH (1.53 g) in THF (37 ml) was cooled to −78° C. nBuLi (9.46 ml, 1.6 M in hexane) was added and the solution was stirred for 5 min. Ethoxyacetic acid ethyl ester (2.0 g) was added and the mixture was stirred at −78° C. for 30 min. The solution was then left to reach r.t. before THF evaporation, EtOAc addition and washing with 1 N aq. HCl, water and brine. After drying over MgSO$_4$ the solvent was evaporated and the crude product was purified by flash chromatography. 0.690 g (26%) of (RS)-2-ethoxy-malonic acid monoethyl ester were obtained as yellow viscous oil. MS 194.1 (100, [M+NH$_4$]$^+$), 177.3 (11, [M+H]$^+$).

66.2

A solution under N$_2$ of (RS)-2-ethoxy-malonic acid monoethyl ester (666 mg, 1.0) in THF (37 ml) was prepared. BOP (2.17 g), 4-aminomethyl-benzonitrile hydrochloride (555 mg) and N-ethyldiisopropylamine (733 mg) were added at 0° C. The ice bath was removed and the reaction was let to stir 24 h. THF was evaporated and the mixture was diluted with EtOAc. This organic phase was washed with a sat. aq. NaHCO$_3$ sol. and with brine. The aqueous phases were extracted with one more portion of EtOAc and dried over MgSO$_4$. The solvent was evaporated. The crude product was purified by flash chromatography. (heptane/EtOAc 3:1 to 2:1). 750 mg (68%) of (RS)-N-(4-cyano-benzyl)-2-ethoxy-malonamic acid ethyl ester were isolated as a yellow oil. MS 308.4 (100, [M+NH$_4$]$^+$), 291.1 (88, [M+H]$^+$).

66.3

A mixture of (RS)-N-(4-cyano-benzyl)-2-ethoxy-malonamic acid ethyl ester (1.97 g) and LiOH (285 mg) in MeOH (14 ml), H$_2$O (7 ml) and THF (14 ml) was stirred 3 h at 60° C. The solvents were evaporated, EtOAc was added and it was washed with HCl 0.1 N, water and brine. The aqueous phases were extracted again with more EtOAc. The combined organic phases were dried (MgSO$_4$) and the solvent was removed to yield (RS)-N-(4-cyano-benzyl)-2-ethoxy-malonamic acid, 1.53 g (86%); of white solid. MS 260.2 (100, [M+H]$^+$), 277.2 (13, [M+NH$_4$]$^+$)

66.4

To a solution under N$_2$ of 1,1'-carbonyldiimidazole (272 mg) in THF (10 ml) was added a solution of (RS)-N-(4-cyano-benzyl)-2-ethoxy-malonamic acid (400 mg) in THF (10 ml). The mixture was stirred for 30 min before addition of a solution of benzamidoxime (228 mg) in THF (20 ml). After stirring 18 h the solvent was evaporated. The crude product was dissolved in EtOAc and extracted with HCl 0.1 N, NaHCO$_3$ and brine. After drying (MgSO$_4$) the solvent was evaporated. The resulting white powder was redissolved in DMF (15 ml) and this solution was heated 5 min in a sealed tube at 140° C. using microwave radiation. DMF was removed, the residue was diluted with EtOAc and washed twice with water. The aqueous phases were extracted with more EtOAc. The combined organic phases were dried over MgSO$_4$ and the solvent was evaporated. Flash chromatography (MeCl$_2$/Et$_2$O, from 100:0 to 95:5) yielded (RS)-N-(4-cyano-benzyl)-2-ethoxy-2-(3-phenyl-[1,2,4]oxadiazol-5-yl)-acetamide, 305 mg (55%); lightly yellow oil. MS 363.1 (100, [M+H]$^+$), 380 (53, [M+NH$_4$]$^+$).

66.5

(RS)-N-(4-Carbamimidoyl-benzyl)-2-ethoxy-2-(3-phenyl-[1,2,4]oxadiazol-5-yl)-acetamide dihydrochloride was prepared from (RS)-N-(4-cyano-benzyl)-2-ethoxy-2-(3-phenyl-[1,2,4]oxadiazol-5-yl)-acetamide (100 mg) according to general procedure D using MeOH as solvent. The product was isolated by crystallization, 125 mg (100%); white solid. MS 380.4 (100, [M+H]$^+$).

Example 67

67.1

To a stirred, cooled (0° C.) dark brown solution of 3.0 g benzimidazole in 20 ml DMF under an argon atmosphere was added portionwise 1.02 g NaH (60% dispersion in mineral oil) within 5 min. The reaction mixture was stirred at r.t. for 45 min, then cooled to 0° C. and treated with 4.22 ml benzyl-2-bromoethyl ether. After 5 min stirring at 0° C., the ice bath was removed and stirring at r.t. was continued for 2 h 30.

The mixture was diluted with EtOAc and washed with H$_2$O. The aqueous phase was extracted with EtOAc. The combined organics were washed with water and brine, dried, filtered and concentrated. The crude product was purified by chromatography on silica using a gradient from cyclohexane to EtOAc to give 3.8 g 1-(2-benzyloxy-ethyl)-1H-benzoimidazole as light yellow solid. MS 253.3 ([M+H]$^+$)

67.2

To a stirred, cooled (−75° C.) light orange solution of 3.79 g 1-(2-benzyloxy-ethyl)-1H-benzoimidazole in 80 ml THF under argon atmosphere was added dropwise 9.4 ml n-butyllithium solution (1.6 M in hexanes) for 15 min (temperature of the solution below −71° C. during the addition; reaction mixture turning to orange). When addition was complete, stirring at −75° C. was continued for 1 h 30. The reaction mixture was then treated with 1.44 ml DMF within 5 min and stirring at −75° C. was continued for 4 h. Then 40 ml of saturated NH$_4$Cl-solution was added to the reaction mixture which was subseqently allowed to warm to r.t. The organic phase was washed with brine, dried (MgSO$_4$), filtered and concentrated. The crude product was purified by chromatography on silica gel using a gradient from cyclohexane to cyclohexane/EtOAc 65:35 to give 1.09 g 1-(2-benzyloxy-ethyl)-1H-benzoimidazole-2-carbaldehyde as viscous yellow oil. MS 281.0 ([M+H]$^+$)

67.3

Using an analogous procedure as described in example 14.1, 1-(2-benzyloxy-ethyl)-1H-benzoimidazole-2-carbaldehyde was converted to (RS)-[1-(2-benzyloxy-ethyl)-1H-benzoimidazol-2-yl]-methoxy-acetic acid. Yellow solid.

67.4

According to general procedure C, (RS)-[1-(2-benzyloxy-ethyl)-1H-benzoimidazol-2-yl]-methoxy-acetic acid was reacted with [(4-aminomethyl-phenyl)-imino-methyl]-carbamic acid benzyl ester dihydrochloride (CAS 172348-75-3) to give (RS)-[1-amino-1-[4-({2-[1-(2-benzyloxy-ethyl)-1H-benzoimidazol-2-yl]-2-methoxy-acetylamino}-methyl)-phenyl]-meth-(Z)-ylidene]-carbamic acid benzyl ester. Off-white gum.

67.5

According to general method E, (RS)-[1-amino-1-[4-({2-[1-(2-benzyloxy-ethyl)-1H-benzoimidazol-2-yl]-2-methoxy-acetylamino}-methyl)-phenyl]-meth-(Z)-ylidene]-carbamic acid benzyl ester was converted to (RS)-2-[1-(2-benzyloxy-ethyl)-1H-benzoimidazol-2-yl]-N-(4-carbamimidoyl-benzyl)-2-methoxy-acetamide acetate (1:1). Off-white solid. MS 472.1 ([M+H]

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed:

1. A compound of the formula (I)

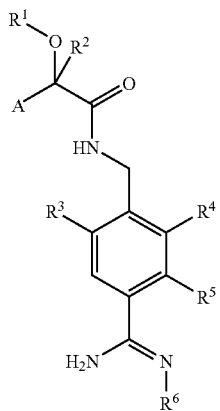

wherein
A is a heterocyclyl selected from the group consisting of pyrazolyl, triazolyl, 1-oxo-1,3-dihydro-isoindolyl, 1,3-dioxo-1,3-dihydro-isoindolyl, oxazolyl, benzimidazolyl, 1,2,4-oxadiazol-5-yl and 2-oxo-2H-pyridinyl, which heterocyclyl is optionally substituted with 1 to 3 substituents independently selected from the group consisting of aryl-$C_{1-7}$alkyl-O—$C_{1-7}$-alkyl, $C_{1-7}$ alkyl, $C_{1-7}$ alkoxy, halogen, aryl, aryl-$C_{1-7}$ alkyl, heteroaryl-$C_{1-7}$ alkyl, heteroaryl, heterocyclyl, tri-$C_{1-7}$ alkyl-silanyl-$C_{1-7}$ alkoxy-$C_{1-7}$ alkyl, $C_{1-7}$ alkyl-SO$_2$—NH, aryl-$C_{1-7}$ alkyl-SO$_2$—NH, aryl-SO$_2$—NH, $C_{1-7}$ alkyl-CO—NH, aryl-$C_{1-7}$ alkyl-CO—NH, aryl-CO—NH, aryl-NH, and heteroaryl-NH, $R^1$ is $C_{1-7}$ alkyl, $R^2$ is H or $C_{1-7}$ alkyl, $R^3$, $R^4$ and $R^5$ independently from each other are selected from the group consisting of $C_{1-7}$alkyl-NH, hydrogen, halogen, carbamoyl-$C_{1-7}$ alkoxy, carboxy-$C_{1-7}$ alkoxy, carboxy-$C_{1-7}$ alkyl-NH, $C_{1-7}$ alkoxy-CO—$C_{1-7}$ alkoxy, $C_{1-7}$ alkoxy-CO—$C_{1-7}$ alkyl-NH, carbamoyl-$C_{1-7}$ alkyl-NH, $C_{1-7}$ alkyl-NH—CO—$C_{1-7}$ alkoxy, $C_{1-7}$ alkyl-NH—CO—$C_{1-7}$ alkyl-NH, aryl-NH—CO—$C_{1-7}$ alkoxy, aryl-NH—CO—$C_{1-7}$ alkyl-NH, carboxy-$C_{1-7}$ alkyl-NH—CO—$C_{1-7}$ alkoxy, carboxy-$C_{1-7}$ alkyl-NH—CO—$C_{1-7}$ alkyl-NH, $C_{1-7}$ alkoxy-CO—$C_{1-7}$ alkyl-NH—CO—$C_{1-7}$ alkoxy, $C_{1-7}$ alkoxy-CO—$C_{1-7}$ alkyl-NH—CO—$C_{1-7}$ alkyl-NH, aryloxy, aryl-NH, aryl-NH—CO—NH, aryl-O—CO—NH, aryl-$C_{1-7}$ alkoxy, aryl-$C_{1-7}$ alkyl-NH, aryl-$C_{1-7}$ alkyl-NH—CO—NH, aryl-$C_{1-7}$ alkoxy-CO—NH, heteroaryloxy, heteroaryl-NH, heteroaryl-NH—CO—NH, heteroaryl-O—CO—NH, heteroaryl-$C_{1-7}$ alkoxy, heteroaryl-$C_{1-7}$ alkyl-NH, heteroaryl-$C_{1-7}$ alkyl-NH—CO—NH, heteroaryl-$C_{1-7}$ alkoxy-CO—NH, aryl-CO—NH, heteroaryl-CO—NH, aryl-$C_{1-7}$ alkyl-CO—NH, and heteroaryl-$C_{1-7}$ alkyl-CO—NH, $R^6$ is hydrogen, hydroxy, aryl-$C_{1-7}$ alkoxy-carbonyl, aryl-carbonyl, or aryloxy-carbonyl, or $R^5$ and $R^6$ are bound together to form a ring and —$R^5$—$R^6$— is —O— or —NH—, and pharmaceutically acceptable salts thereof.

2. The compound of claim 1, wherein A is a heterocyclyl selected from the group consisting of pyrazolyl, triazolyl, 1,3-dioxo-1,3-dihydro-isoindolyl, oxazolyl, benzimidazolyl, and 2-oxo-2H-pyridinyl, said heterocyclyl optionally substituted with 1 to 3 substituents independently selected from the group consisting of $C_{1-7}$ alkyl, aryl, aryl-$C_{1-7}$ alkyl, heteroaryl, tri-$C_{1-7}$ alkyl-silanyl-$C_{1-7}$ alkoxy-$C_{1-7}$ alkyl, aryl-$C_{1-7}$ alkyl-SO$_2$—NH, aryl-SO$_2$—NH, aryl-NH, and heteroaryl-NH.

3. The compound of of claim 2, wherein
A is pyrazolyl which is substituted with 1 to 2 substituents independently selected from the group consisting of $C_{1-7}$ alkyl, aryl, aryl-$C_{1-7}$ alkyl and heteroaryl, or
A is triazolyl which is substituted with 1 to 2 substituents independently selected from the group consisting of $C_{1-7}$ alkyl and aryl, or
A is 1,3-dioxo-1,3-dihydro-isoindolyl, or
A is oxazolyl which is substituted with aryl, or
A is benzimidazolyl which is optionally substituted with $C_{1-7}$ alkyl or tri-$C_{1-7}$ alkyl-silanyl-$C_{1-7}$ alkoxy-$C_{1-7}$ alkyl, or
A is 2-oxo-2H-pyridinyl which is substituted with $C_{1-7}$ alkyl, aryl, aryl-$C_{1-7}$ alkyl-SO$_2$—NH, aryl-SO$_2$—NH, aryl-NH, or heteroaryl-NH.

4. The compound of of claim 3, wherein
A is pyrazolyl which is substituted with 1 to 2 substituents independently selected from the group consisting of $C_{1-7}$ alkyl, aryl and heteroaryl, or
A is triazolyl which is substituted with aryl, or
A is 1,3-dioxo-1,3-dihydro-isoindolyl, or
A is 2-oxo-2H-pyridinyl which is substituted with aryl, aryl-$C_{1-7}$ alkyl-SO$_2$—NH, aryl-NH, or heteroaryl-NH.

5. The compound of of claim 4, wherein A is 3-(5-chloro-2-hydroxy-phenyl)-pyrazol-1-yl, 3-pyridin-4-yl-pyrazol-1-yl, 3-phenyl-[1,2,4]triazol-1-yl, 3-(2-hydroxy-phenyl)-4-methyl-pyrazol-1-yl, 1,3-dioxo-1,3-dihydro-isoindol-2-yl, 2-oxo-3-phenylmethanesulfonylamino-2H-pyridin-1-yl, 2-oxo-3-(pyridin-3-ylamino)-2H-pyridin-1-yl, 2-oxo-3-phenylamino-2H-pyridin-1-yl, or 2-oxo-6-phenyl-1,2-dihydro-pyridin-3-yl.

6. The compound of claim 5, wherein $R^1$ is methyl or ethyl.

7. The compound of claim 6, wherein $R^1$ is ethyl.

8. The compound of claim 7, wherein $R^2$ is hydrogen.

9. The compound of claim 8, wherein $R^3$, $R^4$ and $R^5$ independently from each other are selected from the group consisting of hydrogen, halogen, and carbamoyl-$C_{1-7}$ alkoxy.

10. The compound of claim 9, wherein $R^3$ is hydrogen or halogen.

11. The compound of claim 10, wherein $R^3$ is hydrogen.

12. The compound of claim 11, wherein $R^4$ is hydrogen, halogen, or carbamoyl-$C_{1-7}$ alkoxy.

13. The compound of claim 12, wherein $R^4$ is hydrogen, fluorine, or carbamoyl-methoxy.

14. The compound of claim 13, wherein $R^5$ is hydrogen or halogen.

15. The compound of claim 14, wherein $R^5$ is hydrogen.

16. The compound of claim 15, wherein $R^6$ is hydrogen, hydroxy, or aryl-$C_{1-7}$ alkoxy-carbonyl.

17. The compound of claim 16, wherein $R^6$ is hydrogen.

18. The compound of claim 13, wherein $R^5$ and $R^6$ are bound together and —$R^5$—$R^6$— is —O— or —NH—.

19. The compound of claim 1, selected from the group consisting of
(RS)-N-(4-carbamimidoyl-benzyl)-2-ethoxy-2-[3-(4-methoxy-phenyl)-pyrazol-1-yl]-acetamide hydrochloride,
(RS)-N-(4-carbamimidoyl-benzyl)-2-ethoxy-2-(3-phenyl-pyrazol-1-yl)-acetamide hydrochloride, (RS)-N-(4-carbamimidoyl-benzyl)-2-ethoxy-2-(5-methyl-3-pyridin-3-yl-pyrazol-1-yl)-acetamide acetate, and (RS)-2-[3-(2-benzyloxy-5-chloro-phenyl)-pyrazol-1-yl]-N-(4-carbamimidoyl-benzyl)-2-ethoxy-acetamide hydrochloride, (RS)-N-(4-carbamimidoyl-benzyl)-2-[3-(5-chloro-2-hydroxy-phenyl)-pyrazol-1-yl]-2-ethoxy-acetamide hydrochloride, (RS)-2-[3-(3-amino-phenyl)-pyrazol-1-yl]-N-(4-carbamimidoyl-benzyl)-2-ethoxy-acetamide hydrochloride, (RS)-2-[3-(3-acetylamino-phenyl)-pyrazol-1-yl]-N-(4-carbamimidoyl-benzyl)-2-ethoxy-acetamide hydrochloride, (RS)-N-(4-carbamimidoyl-benzyl)-2-ethoxy-2-[3-(3-methanesulfonylamino-phenyl)-pyrazol-1-yl]-acetamide hydrochloride, (RS)-[amino-(4-{[2-ethoxy-2-(3-pyridin-4-yl-pyrazol-1-yl)-acetylamino]-methyl}-phenyl)-methylene]-carbamic acid benzyl ester, (RS)-N-(4-carbamimidoyl-benzyl)-2-ethoxy-2-(3-pyridin-4-yl-pyrazol-1-yl)-acetamide acetate, (RS)-2-ethoxy-N-[4-(N-hydroxycarbamimidoyl)-benzyl]-2-(3-phenyl-[1,2,4]triazol-1-yl)-acetamide, (RS)-N-(4-carbamimidoyl-benzyl)-2-ethoxy-2-(3-phenyl-[1,2,4]triazol-1-yl)-acetamide acetate, (RS)-2-[3-(2-benzyloxy-phenyl)-4-methyl-pyrazol-1-yl]-2-ethoxy-N-[4-(N-hydroxycarbamimidoyl)-benzyl]-acetamide, (RS)-N-(4-carbamimidoyl-benzyl)-2-ethoxy-2-[3-(2-hydroxy-phenyl)-4-methyl-pyrazol-1-yl]-acetamide acetate, (RS)-N-(4-carbamimidoyl-benzyl)-2-ethoxy-2-[3-(2-carbamoylmethoxy-phenyl)-4-methyl-pyrazol-1-yl]-2-ethoxy-acetamide acetate, (RS)-[2-(1-{ethoxy-[4-(N-hydroxycarbamimidoyl)-benzylcarbamoyl]-methyl}-4-methyl-1H-pyrazol-3-yl)-phenoxy]-acetic acid ethyl ester, (RS)-(2-{1-[(4-carbamimidoyl-benzylcarbamoyl)-ethoxy-methyl]-4-methyl-1H-pyrazol-3-yl}-phenoxy)-acetic acid ethyl ester acetate, (RS)-(2-{1-[(4-carbamimidoyl-benzylcarbamoyl)-ethoxy-methyl]-4-methyl-1H-pyrazol-3-yl}-phenoxy)-acetic acid acetate, (RS)-[1-amino-1-(4-{[2-(1,3-dioxo-1,3-dihydro-isoindol-2-yl)-2-ethoxy-acetylamino]-methyl}-phenyl)-meth-(Z)-ylidene]-carbamic acid benzyl ester, (RS)-N-(4-carbamimidoyl-benzyl)-2-(1,3-dioxo-1,3-dihydro-isoindol-2-yl)-2-ethoxy-acetamide acetate, (RS)-2-(1-benzyl-1H-pyrazol-3-yl)-N-(4-carbamimidoyl-benzyl)-2-methoxy-acetamide hydrochloride, (RS)-N-(4-carbamimidoyl-benzyl)-2-ethoxy-2-(2-phenyl-oxazol-4-yl)-acetamide acetate, (RS)-2-ethoxy-N-[4-(N-hydroxycarbamimidoyl)-benzyl]-2-(5-methyl-1-phenyl-1H-[1,2,4]triazol-3-yl)-acetamide, (RS)-N-(4-carbamimidoyl-benzyl)-2-ethoxy-2-(5-methyl-1-phenyl-1H-[1,2,4]triazol-3-yl)-acetamide acetate, (RS)-N-(4-carbamimidoyl-benzyl)-2-methoxy-2-(1-methyl-1H-benzoimidazol-2-yl)-acetamide acetate, (RS)-[1-amino-1-[4-({2-methoxy-2-[1-(2-trimethylsilanyl-ethoxymethyl)-1H-benzoimidazol-2-yl]-acetylamino}-methyl)-phenyl]-meth-(E)-ylidene]-carbamic acid benzyl ester, (RS)-[1-amino-1-(4-{[2-(1H-benzoimidazol-2-yl)-2-methoxy-acetylamino]-methyl}-phenyl)-meth-(E)-ylidene]-carbamic acid benzyl ester, (RS)-2-(1H-benzoimidazol-2-yl)-N-(4-carbamimidoyl-benzyl)-2-methoxy-acetamide acetate, (RS)-N-(4-carbamimidoyl-benzyl)-2-ethoxy-2-(2-oxo-3-phenylmethanesulfonylamino-2H-pyridin-1-yl)-acetamide acetate, (RS)-2-(3-benzenesulfonylamino-2-oxo-2H-pyridin-1-yl)-N-(4-carbamimidoyl-benzyl)-2-ethoxy-acetamide acetate, (RS)-N-(4-carbamimidoyl-benzyl)-2-ethoxy-2-(2-oxo-3-phenylamino-2H-pyridin-1-yl)-acetamide acetate, (RS)-{amino-[4-({2-ethoxy-2-[3-(3-methoxy-phenylamino)-2-oxo-2H-pyridin-1-yl]-acetylamino}-methyl)-phenyl]-methylene}-carbamic acid benzyl ester, (RS)-N-(4-carbamimidoyl-benzyl)-2-ethoxy-2-[3-(3-methoxy-phenylamino)-2-oxo-2H-pyridin-1-yl]-acetamide acetate, (RS)-{amino-[4-({2-ethoxy-2-[3-(3-fluoro-phenylamino)-2-oxo-2H-pyridin-1-yl]-acetylamino}-methyl)-phenyl]-methylene}-carbamic acid benzyl ester, (RS)-N-(4-carbamimidoyl-benzyl)-2-ethoxy-2-[3-(3-fluoro-phenylamino)-2-oxo-2H-pyridin-1-yl]-acetamide acetate, (RS)-{amino-[4-({2-ethoxy-2-[2-oxo-3-(pyridin-3-ylamino)-2H-pyridin-1-yl]-acetylamino}-methyl)-phenyl]-methylene}-carbamic acid benzyl ester, (RS)-N-(4-carbamimidoyl-benzyl)-2-ethoxy-2-[2-oxo-3-(pyridin-3-ylamino)-2H-pyridin-1-yl]-acetamide acetate, (RS)-N-[2-chloro-4-(N-hydroxycarbamimidoyl)-benzyl]-2-ethoxy-2-(2-oxo-3-phenylamino-2H-pyridin-1-yl)-acetamide, (RS)-N-(4-carbamimidoyl-2-chloro-benzyl)-2-ethoxy-2-(2-oxo-3-phenylamino-2H-pyridin-1-yl)-acetamide acetate, (RS)-N-[3-chloro-4-(N-hydroxycarbamimidoyl)-benzyl]-2-ethoxy-2-(2-oxo-3-phenylamino-2H-pyridin-1-yl)-acetamide, (RS)-N-(4-carbamimidoyl-3-chloro-benzyl)-2-ethoxy-2-(2-oxo-3-phenylamino-2H-pyridin-1-yl)-acetamide acetate, (RS)-2-ethoxy-N-[2-fluoro-4-(N-hydroxycarbamimidoyl)-benzyl]-2-(2-oxo-3-phenylamino-2H-pyridin-1-yl)-acetamide, (RS)-N-(4-carbamimidoyl-2-fluoro-benzyl)-2-ethoxy-2-(2-oxo-3-phenylamino-2H-pyridin-1-yl)-acetamid acetate, (RS)-2-ethoxy-N-[3-fluoro-4-(N-hydroxycarbamimidoyl)-benzyl]-2-(2-oxo-3-phenylamino-2H-pyridin-1-yl)-acetamide, (RS)-N-(4-carbamimidoyl-3-fluoro-benzyl)-2-ethoxy-2-(2-oxo-3-phenylamino-2H-pyridin-1-yl)-acetamide acetate, (RS)-N-[2,6-difluoro-4-(N-hydroxycarbamimidoyl)-benzyl]-2-ethoxy-2-(2-oxo-3-phenylamino-2H-pyridin-1-yl)-acetamide, (RS)-N-(4-carbamimidoyl-2,6-difluoro-benzyl)-2-ethoxy-2-(2-oxo-3-phenylamino-2H-pyridin-1-yl)-acetamide acetate, (RS)-N-(3-amino-benzo[d]isoxazol-6-ylmethyl)-2-ethoxy-2-(2-oxo-3-phenylamino-2H-pyridin-1-yl)-acetamide, (RS)-N-(3-amino-1H-indazol-6-ylmethyl)-2-ethoxy-2-(2-oxo-3-phenylamino-2H-pyridin-1-yl)-acetamide, (RS)-N-[2-carbamoylmethoxy-4-(N-hydroxycarbamimidoyl)-benzyl]-2-ethoxy-2-(2-oxo-3-phenylamino-2H-pyridin-1-yl)-acetamide,
(RS)-N-(4-arbamimidoyl-2-carbamoylmethoxy-benzyl)-2-ethoxy-2-(2-oxo-3-phenylamino-2H-pyridin-1-yl)-acetamide acetate,
(RS)-N-(4-carbamimidoyl-benzyl)-2-ethoxy-2-(6-methyl-2-oxo-1,2-dihydro-pyridin-3-yl)-acetamide hydrochloride, and
(RS)-N-(4-carbamimidoyl-benzyl)-2-ethoxy-2-(2-oxo-6-phenyl-1,2-dihydro-pyridin-3-yl)-acetamide hydrochloride,
(RS)-N-(4-carbamimidoyl-benzyl)-2-ethoxy-2-(4-fluoro-1,3-dioxo-1,3-dihydro-isoindol-2-yl)-acetamide acetate,
(RS)-N-(4-carbamimidoyl-benzyl)-2-ethoxy-2-(5-methyl-1,3-dioxo-1,3-dihydro-isoindol-2-yl)-acetamide,
(RS)-N-(4-carbamimidoyl-benzyl)-2-ethoxy-2-(4-methyl-1,3-dioxo-1,3-dihydro-isoindol-2-yl)-acetamide,
(RS)-N-(4-carbamimidoyl-benzyl)-2-(4,7-difluoro-1,3-dioxo-1,3-dihydro-isoindol-2-yl)-2-ethoxy-acetamide acetate,
(RS)-2-(5-tert-butyl-1,3-dioxo-1,3-dihydro-isoindol-2-yl)-N-(4-carbamimidoyl-benzyl)-2-ethoxy-acetamide,
(RS)-N-(4-carbamimidoyl-benzyl)-2-ethoxy-2-(6-methyl-1-oxo-1,3-dihydro-isoindol-2-yl)-acetamide acetate,
(RS)-N-(4-carbamimidoyl-benzyl)-2-ethoxy-2-(5-methyl-1-oxo-1,3-dihydro-isoindol-2-yl)-acetamide acetate,
(RS)-N-(4-carbamimidoyl-benzyl)-2-ethoxy-2-(4-fluoro-1-oxo-1,3-dihydro-isoindol-2-yl)-acetamide acetate,
(RS)-N-(4-carbamimidoyl-benzyl)-2-(4,7-difluoro-1-oxo-1,3-dihydro-isoindol-2-yl)-2-ethoxy-acetamide acetate,
(RS)-N-(4-carbamimidoyl-benzyl)-2-ethoxy-2-(4-methyl-1-oxo-1,3-dihydro-isoindol-2-yl)-acetamide acetate,
(RS)-N-(4-carbamimidoyl-benzyl)-2-ethoxy-2-(7-methyl-1-oxo-1,3-dihydro-isoindol-2-yl)-acetamide acetate,
(RS)-N-[4-carbamimidoyl-2-(2-fluoro-benzylamino)-benzyl]-2-ethoxy-2-(4-methyl-1-oxo-1,3-dihydro-isoindol-2-yl)-acetamide acetate,
(RS)-N-[4-carbamimidoyl-2-(2-fluoro-benzylamino)-benzyl]-2-ethoxy-2-(7-methyl-1-oxo-1,3-dihydro-isoindol-2-yl)-acetamide acetate,
(RS)-N-[4-carbamimidoyl-2-(2-fluoro-benzylamino)-benzyl]-2-ethoxy-2-(4-fluoro-1-oxo-1,3-dihydro-isoindol-2-yl)-acetamide acetate,
(RS)-N-(4-carbamimidoyl-2-ethylamino-benzyl)-2-ethoxy-2-(4-fluoro-1-oxo-1,3-dihydro-isoindol-2-yl)-acetamide acetate,
(RS)-4-[(5-carbamimidoyl-2-{[2-(4-fluoro-1-oxo-1,3-dihydro-isoindol-2-yl)-2-methoxy-acetylamino]-methyl}-phenylamino)-methyl]-benzoic acid methyl ester acetate,
(RS)-N-(4-carbamimidoyl-2-ethylamino-benzyl)-2-ethoxy-2-(4-methyl-1-oxo-1,3-dihydro-isoindol-2-yl)-acetamide acetate,
(RS)-N-[4-carbamimidoyl-2-(2-fluoro-benzylamino)-benzyl]-2-(6-chloro-1-oxo-1,3-dihydro-isoindol-2-yl)-2-ethoxy-acetamide acetate,
(RS)-N-(4-carbamimidoyl-2-ethylamino-benzyl)-2-(6-chloro-1-oxo-1,3-dihydro-isoindol-2-yl)-2-ethoxy-acetamide acetate,
(RS)-N-(4-carbamimidoyl-2-ethylamino-benzyl)-2-ethoxy-2-(5-methoxy-1-oxo-1,3-dihydro-isoindol-2-yl)-acetamide acetate,
(RS)-N-(2-amino-4-carbamimidoyl-benzyl)-2-ethoxy-2-(5-methoxy-1-oxo-1,3-dihydro-isoindol-2-yl)-acetamide acetate,
(RS)-N-(4-carbamimidoyl-2-ethylamino-benzyl)-2-ethoxy-2-(1-oxo-6-piperidin-1-yl-1,3-dihydro-isoindol-2-yl)-acetamide acetate,
(RS)-N-[4-carbamimidoyl-2-(2-fluoro-benzylamino)-benzyl]-2-ethoxy-2-(1-oxo-6-piperidin-1-yl-1,3-dihydro-isoindol-2-yl)-acetamide acetate,
(RS)-N-(4-carbamimidoyl-2-ethylamino-benzyl)-2-ethoxy-2-(1-oxo-6-pyrrolidin-1-yl-1,3-dihydro-isoindol-2-yl)-acetamide hydrochloride,
(RS)-N-[4-carbamimidoyl-2-(2-fluoro-benzylamino)-benzyl]-2-ethoxy-2-(1-oxo-6-pyrrolidin-1-yl-1,3-dihydro-isoindol-2-yl)-acetamide acetate,
(RS)-N-[4-carbamimidoyl-2-(2-fluoro-benzylamino)-benzyl]-2-ethoxy-2-(4-fluoro-1,3-dioxo-1,3-dihydro-isoindol-2-yl)-acetamide acetate,
(RS)-N-[4-carbamimidoyl-2-(2-fluoro-benzylamino)-benzyl]-2-ethoxy-2-(5-methyl-1,3-dioxo-1,3-dihydro-isoindol-2-yl)-acetamide acetate,
(RS)-4-[(5-carbamimidoyl-2-{[2-ethoxy-2-(5-methyl-1,3-dioxo-1,3-dihydro-isoindol-2-yl)-acetylamino]-methyl}-phenylamino)-methyl]-benzoic acid methyl ester acetate,
(RS)-N-(4-carbamimidoyl-2-carbamoylmethoxy-benzyl)-2-ethoxy-2-(4-methyl-1-oxo-1,3-dihydro-isoindol-2-yl)-acetamide acetate,
(RS)-N-(4-carbamimidoyl-2-carbamoylmethoxy-benzyl)-2-ethoxy-2-(5-methoxy-1-oxo-1,3-dihydro-isoindol-2-yl)-acetamide acetate,
(RS)-N-(4-carbamimidoyl-2-methylcarbamoylmethoxy-benzyl)-2-ethoxy-2-(5-methoxy-1-oxo-1,3-dihydro-isoindol-2-yl)-acetamide acetate,
(RS)-N-(4-carbamimidoyl-benzyl)-2-ethoxy-2-(3-phenyl-[1,2,4]oxadiazol-5-yl)-acetamide dihydrochloride,
and pharmaceutically acceptable salts thereof.

20. A process for the manufacture of compounds of claim 1, which process comprises converting the nitrile group in a compound of formula (II)

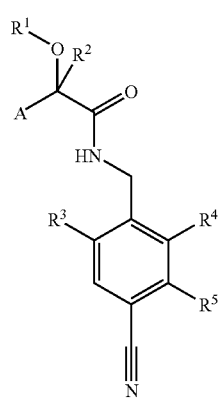

(II)

wherein $R^1$, $R^2$, $R^3$, $R^4$, $R^5$ and A have the values in claim 1, into a carbamimidoyl group, or into a N-hydroxy-carbamimidoyl group, or which process comprises coupling a compound of formula (III) with a compound of formula (IV)

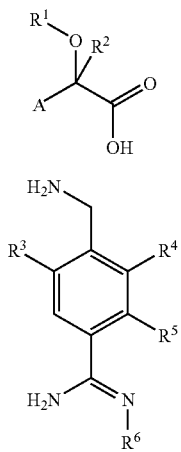

(III)

(IV)

wherein $R^1$, $R^2$, $R^3$, $R^4$, $R^5$, $R^6$ and a are as defined in claim 1, and, if desired, converting an obtained compound of formula (I) into a pharmaceutically acceptable salt.

21. A pharmaceutical composition comprising a compound of the formula

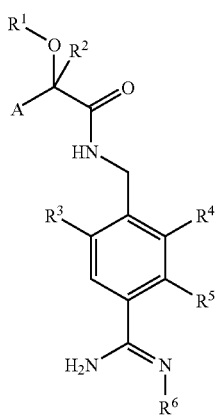

(I)

wherein

A is a heterocyclyl selected from the group consisting of pyrazolyl, triazolyl, 1-oxo-1,3-dihydro-isoindolyl, 1,3-dioxo-1,3-dihydro-isoindolyl, oxazolyl, benzimidazolyl, 1,2,4-oxadiazol-5-yl and 2-oxo-2H-pyridinyl, which heterocyclyl is optionally substituted with 1 to 3 substituents independently selected from the group consisting of aryl-$C_{1-7}$alkyl-O—$C_{1-7}$-alkyl, $C_{1-7}$ lower-alkyl, $C_{1-7}$ lower-alkoxy, halogen, aryl, aryl-$C_{1-7}$-lower-alkyl, heteroaryl-$C_{1-7}$ lower-alkyl, heteroaryl, heterocyclyl, tri-$C_{1-7}$ lower-alkyl-silanyl-$C_{1-7}$ lower-alkoxy-$C_{1-7}$ lower-alkyl, $C_{1-7}$ lower-alkyl-$SO_2$—NH, aryl-$C_{1-7}$ lower-alkyl-$SO_2$—NH, aryl-$SO_2$—NH, $C_{1-7}$ lower-alkyl-CO—NH, aryl-$C_{1-7}$ lower-alkyl-CO—NH, aryl-CO—NH, aryl-NH, and heteroaryl-NH, $R^1$ is $C_{1-7}$ lower-alkyl, $R^2$ is H or $C_{1-7}$ lower-alkyl, $R^3$, $R^4$ and $R^5$ independently from each other are selected from the group consisting of $C_{1-7}$alkyl-NH, hydrogen, halogen, carbamoyl-$C_{1-7}$ lower-alkoxy, carboxy-$C_{1-7}$ lower-alkoxy, carboxy-$C_{1-7}$ lower-alkyl-NH, $C_{1-7}$ lower-alkoxy-CO—$C_{1-7}$ lower-alkoxy, $C_{1-7}$ lower-alkoxy-CO—$C_{1-7}$ lower-alkyl-NH, carbamoyl-$C_{1-7}$ lower-alkyl-NH, $C_{1-7}$ lower-alkyl-NH—CO—$C_{1-7}$ lower-alkoxy, $C_{1-7}$ lower-alkyl-NH—CO—$C_{1-7}$ lower-alkyl-NH, aryl-NH—CO—$C_{1-7}$ lower-alkoxy, aryl-NH—CO—$C_{1-7}$ lower-alkyl-NH, carboxy-$C_{1-7}$ lower-alkyl-NH—CO—$C_{1-7}$ lower-alkoxy, carboxy-$C_{1-7}$ lower-alkyl-NH—CO—$C_{1-7}$ lower-alkyl-NH, $C_{1-7}$ lower-alkoxy-CO—$C_{1-7}$ lower-alkyl-NH—CO—$C_{1-7}$ lower-alkoxy, $C_{1-7}$ lower-alkoxy-CO—$C_{1-7}$ lower-alkyl-NH—CO—$C_{1-7}$ lower-alkyl-NH, aryloxy, aryl-NH, aryl-NH—CO—NH, aryl-O—CO—NH, aryl-$C_{1-7}$ lower-alkoxy, aryl-$C_{1-7}$ lower-alkyl-NH, aryl-$C_{1-7}$ lower-alkyl-NH—CO—NH, aryl-$C_{1-7}$ lower-alkoxy-CO—NH, heteroaryloxy, heteroaryl-NH, heteroaryl-NH—CO—NH, heteroaryl-O—CO—NH, heteroaryl-$C_{1-7}$ lower-alkoxy, heteroaryl-$C_{1-7}$ lower-alkyl-NH, heteroaryl-$C_{1-7}$ lower-alkyl-NH—CO—NH, heteroaryl-$C_{1-7}$ lower-alkoxy-CO—NH, aryl-CO—NH, heteroaryl-CO—NH, aryl-$C_{1-7}$ lower-alkyl-CO—NH, and heteroaryl-$C_{1-7}$ lower-alkyl-CO—NH, $R^6$ is hydrogen, hydroxy, aryl-$C_{1-7}$ lower-alkoxy-carbonyl, aryl-carbonyl, or aryloxy-carbonyl, or $R^5$ and $R^6$ are bound together to form a ring and —$R^5$—$R^6$— is —O— or —NH—, and pharmaceutically acceptable salts thereof, and a pharmaceutically acceptable carrier and/or adjuvant.

* * * * *